ns407B2

United States Patent
Wu et al.

(10) Patent No.: US 9,023,407 B2
(45) Date of Patent: May 5, 2015

(54) PLANT EXTRACT FOR TREATING DIABETES AND PROCESS FOR MAKING SAME

(75) Inventors: Rey-Yuh Wu, New Taipei (TW); Hui-Ling Chen, New Taipei (TW); Yu-Yuan Wu, New Taipei (TW); Lung-Yu Kuan, New Taipei (TW); Chao-Tsen Lu, New Taipei (TW); Shoei-Sheng Lee, Taichung (TW)

(73) Assignee: Development Center for Biotechnology, New Taipei (TW)

( * ) Notice: Subject to any disclaimer, the term of this patent is extended or adjusted under 35 U.S.C. 154(b) by 234 days.

(21) Appl. No.: 13/569,656

(22) Filed: Aug. 8, 2012

(65) Prior Publication Data
US 2013/0040004 A1    Feb. 14, 2013

(51) Int. Cl.
*A61K 36/906*    (2006.01)

(52) U.S. Cl.
CPC ........... *A61K 36/906* (2013.01); *A61K 2236/39* (2013.01)

(58) Field of Classification Search
USPC ........................................ 424/756
IPC ..................... A61K 39/906,36/9064
See application file for complete search history.

(56) References Cited

U.S. PATENT DOCUMENTS

2006/0141069 A1    6/2006  Pushpangadan et al.
2011/0195139 A1*   8/2011  Wu et al. ........................ 424/756
2011/0217394 A1*   9/2011  West et al. ..................... 424/732

FOREIGN PATENT DOCUMENTS

WO    WO 2006/082481 A1    8/2006

OTHER PUBLICATIONS

Omata et al. Flavour and Fragrance J. 1991. vol. 6, pp. 217-220.*
Matsumoto et al. J. Essent. Oil Res. 1993 vol. 5, pp. 123-133.*
Lu et al. African J. Biotechnol. 2009. vol. 8, No. 20, pp. 5373-5377.*
Dhawan, B.N., et al., Screening of Indian Plants for Biological Activity: Part VI, Indian Journal of Experimental Biology, vol. 15, Mar. 1977, pp. 208-219.
Bhandary, M.J., et al., Medical ethnobotany of the Siddis of Uttara Kannada district, Karnataka India, Journal of Bthnopharmacology 47, 1995, pp. 149-158.

* cited by examiner

*Primary Examiner* — Chris R Tate
(74) *Attorney, Agent, or Firm* — Wolf, Greenfield & Sacks, P.C.

(57) ABSTRACT

The present invention relates to a plant extract for treating diabetes and a process for making same. The plant extract of the invention is prepared from an overground part of *Hedychium coronarium Koenig*, which has the efficacies of lowering blood glucose, increasing insulin levels, reducing insulin resistance and treating and/or preventing diabetes without overly reducing blood glucose in a subject, i.e., not reducing blood glucose in a fasting subject. Also provided herein is a method for treating diabetes in a subject in need thereof comprising administering an effective amount of the plant extract to the subject.

25 Claims, 19 Drawing Sheets

PLANT EXTRACT FOR TREATING DIABETES AND PROCESS FOR MAKING SAME

RELATED APPLICATION

This application claims priority to Taiwan Patent Application No. 100128239, filed on Aug. 8, 2011, the content of which is hereby incorporated by reference in its entirety.

TECHNOLOGY FIELD

The present invention relates to a plant extract for treating diabetes and a process for making same. In particular, the plant extract is prepared from one or more overground parts of *Hedychium coronarium Koenig*. Such a plant extract has the efficacies of lowering blood glucose, increasing insulin levels and/or reducing insulin resistance, and thus can be used to treat and/or prevent diabetes.

BACKGROUND OF THE INVENTION

Diabetes is a chronic disease due to deficiency in the production of insulin by the pancreas or ineffectiveness of the insulin produced. The disease results in increased levels of glucose in the blood and then causes damages to many of the body's tissues or organs, in particular the blood vessels and the nerves.

There are two forms of diabetes, type I diabetes and type II diabetes. Type I diabetes is also called insulin-dependent diabetes mellitus (IDDM). The IDDM patients have destruction of pancreatic beta cells which causes failure to produce insulin and is vital to the patient's life. Type I diabetes develops frequently in children and adolescents, and therefore was previously known as juvenile diabetes. However, it is being now increasingly noted in adults. Type I diabetic patients must administer insulin by injection for their entire life time. Type II diabetes, also called non-insulin-dependent diabetes mellitus (NIDDM), is strongly familial; however, environmental factors also play an important role in the development of the disease. Healthy diet, physical exercise and avoidance of overweight may prevent the disease and control its progress. Type II diabetic patients need to take medicaments for satisfactory blood glucose control, and some of the patients need insulin for reducing their blood glucose levels.

Several complications are associated with diabetes, such as retinopathy, nerves damages, feet pains, varicose vein, edemas, blood circulation dysfunction, walking difficulties, liver dysfunction, hyperlcholesterolemia, proteinuria, hyperlipidemia, prostate enlargement, and hypertension. Controlling blood sugar levels will help ensure this disease under control and reduce the risk of complications.

Currently used medicaments for treatment of diabetes include sulfonylureas, meglitinides, biguanides, thiazolidinediones, and alpha glucosidase inhibitors, which however have several limitations, such as adverse effects and high rates of secondary failure. In addition, compositions comprising natural components having efficacies for treating diabetes have been reported. For example, U.S. Pat. No. 6,042,834, describes an herbal composition, comprising 15 percent by weight of dried, powdered seeds of *Trigonella foenum-graecum*; 23 percent by weight of dried, powdered seeds of *Nigella sativa*; 10 percent by weight of dried, powdered leaves of *Origanum vulgare*; 10 percent by weight of dried, powdered sap of *Rosmarinus officinalis*; 15 percent by weight of dried, powdered beans of *Lupinus tennis*; 12 percent by weight of dried, powdered black leaves of *Lawsonia inennis*; and 15 percent by weight of dried, powdered seeds of *Foeniculum vulgare*. Chinese Patent Publication No. 1243559 provides a herbal composition, comprising the plant of centaury (*Centauri herba*) 12.3% by wt., the root of dandelion (*Teraxaci radix*) 9.7% by wt., the fruit of juniper (*Juniperi communis fructus*) 6.2% by wt., the plant of nettle (*Urticae herba*) 7.4% by wt., the root of nettle (*Urticae radix*) 7.0% by wt., the root of chicory (Cichorii radix) 17.7% by wt., the leaf of black mulberry (*Morus nigra folium*) 7.4% by wt., the flower of yarrow (*Achilleae millefolii flos*) 3.5% by wt., the leaf of bilberry (*Vaccinii myritilli folium*) 6.6% by wt., the pod of beans (*Phaseoli fructus sine semeni*) 14.4% by wt., and the root of valerian (*Valerianae officinalis radix*) 7.8% by wt. Taiwan Patent Publication No. 201100088 discloses a multifunctional food composition with multiple components to improve hyperlipidemia, hyperglycemia and fatty liver, comprising bitter gourd, green algae, Licorice, and soybean powers. U.S. Patent Publication No. 2011159127 discloses an extract of *Tonna sinensis* from supercritical fluid extraction for treatments of diabetes and metabolic diseases, which is prepared by the steps of (a) drying the leaves of *T. sinensis*; (b) pulverizing the leaves as particles; and (c) extracting the particles with supercritical carbon dioxide to obtain the *T. sinensis* extract. The *T. sinensis* extract not only can decrease blood sugar level, but also promotes lipid degradation, inhibits the formation of huge lipid droplet and improves the metabolic symptoms.

In addition, WO2006/082481 discloses that rhizomes of *Hedychium spicatum* are useful for the treatment of Tinea infections. U.S. patent Publication No. 20060141069 discloses a synergistic antipyretic formulation comprising extracts of plants *Berberis aristata, Tinospora cordifolia, Alstonia scholaris, Andrographis paniculata* and *Hedychium spicatum*. Further, it has been reported that an essential oil extracted from the rhizome of *Hedychium spicatum* is hypoglycemic (Indian Journal of Expertmental Biology, Vol. 15, March 1977, pp. 208-219), and a mixture of the dried rhizome powder of *Hedychium coronarium Koening* with milk is traditionally used at some area in India to treat diabetes (J. Ethnopharmacol., 47(3): 149-158, 1995).

BRIEF SUMMARY OF THE INVENTION

The present disclosure is based on the development of novel preparation processes for making *Hedychium coronarium Koenig* extracts (HC extracts), which, unexpectedly, exhibited high anti-diabetes activities, such as lowering blood glucose levels, increasing insulin levels, and reducing insulin resistance. Thus, such HC extracts can be used for treating diabetes, including both type I and type II diabetes. Particularly, the extracts prepared by the methods described herein do not overly reduce blood glucose in a subject, such as in a fasting subject, and thus may be used to alleviate or prevent hypoglycermia, a side effect associated with conventional diabetes treatment.

Accordingly, described herein are methods for preparing anti-diabetes HC extracts, HC extracts thus prepared; and uses thereof in treating diabetes (both type I and type II diabetes).

In one aspect, the present disclosure provides processes for preparing a *Hedychium coronarium Koenig* extract (HC extract) useful for treating diabetes (preparation process I).

In some embodiments, the preparation process described herein comprises:

(a) extracting an overground part of *Hedychium coronarium Koenig* with a first solvent to obtain a first extract, wherein the first solvent is petroleum ether, n-hexane, dichloromethane, trichloromethane, ethyl acetate, acetone, ethanol at a concentration of at least 70% (v/v in water), or any combination thereof; and (b) loading the first extract onto an ion exchange chromatography column;

(c) washing the ion exchange chromatography column with a solution of water and ethanol at a volume ratio from 1:1 to 1:9, and (d) eluting the first ion exchange chromatography with ethanol at a concentration of at least 70% (v/v in water), to produce the HC extract.

In other embodiments, the preparation process comprises:

(a) extracting an overground part of *Hedychium coronarium Koenig* with a first solvent to obtain a first residue and a first extract, wherein the first solvent is petroleum ether, n-hexane, dichloromethane, trichloromethane, ethyl acetate, acetone, ethanol at a concentration of at least 70% (v/v in water), or any combination thereof;

(b) extracting the first residue with a second solvent to obtain a second extract, wherein the second solvent is water, ethanol at a concentration of up to 50% (v/v in water), methanol, butanol, iso-butanol, acetone at an concentration of up to 80% (v/v in water), or any combination thereof; and (c) loading the second extract onto an ion exchange chromatography column;

(d) washing the ion exchange chromatography column with water; and (e) eluting the ion exchange chromatography column with ethanol at a concentration of 5-50% (v/v in water) to produce the HC extract.

In yet other embodiments, the preparation process described herein comprises:

(a) extracting an overground part of *Hedychium coronarium Koenig* with a first solvent to obtain a first extract and a first residue, wherein the first solvent is petroleum ether, n-hexane, dichloromethane, trichloromethane, ethyl acetate, acetone, ethanol at a concentration of 70-100% (v/v in water), or any combination thereof;

(b) extracting the first residue with a second solvent to obtain a second extract, wherein the second solvent is water, ethanol at a concentration of up to 50% (v/v in water), methanol, butanol, iso-butanol, acetone at an concentration of up to 80% (v/v in water), or any combination thereof;

(c) subjecting the first extract and the second extract to ion exchange chromatography to obtain a first eluate and a second eluate, respectively, wherein the first eluate is obtained by a process comprising:

loading the first extract onto a first ion exchange chromatography column;

washing the first ion exchange chromatography column a solution of water and ethanol at a volume ratio from 1:1 to 1:9, and eluting the first ion exchange chromatography with ethanol at a concentration of at least 70% (v/v in water) to produce the first eluate; and wherein the second eluate is obtained by a process comprising:

loading the second extract onto a second ion exchange chromatography column;

washing the second ion exchange chromatography column water, and eluting the second ion exchange chromatography column with ethanol at a concentration of 5-50% (v/v in water) to produce the second eluate;

and (d) combining the first eluate and the second eluate to obtain the HC extract.

In any of the preparation processes described herein, the first solvent can be 95% ethanol (v/v in water) and/or the second solvent can be ethanol at a concentration of up to 50% (v/v in water).

In another aspect, the present disclosure provides an extract of *Hedychium coronarium Koenig*, which can be prepared by any of the preparation processes described herein.

In some embodiments, the HC extract exhibits four peaks at retention times (i) 8.55-10.34 minutes, (ii) 17.64-21.34 minutes, (iii) 20.55-24.86 minutes, and (iv) 42.91-51.92 minutes in a first high performance liquid chromatography (HPLC) analysis using a linear gradient of methanol and water, wherein the first HPLC analysis is carried out under the following conditions: mobile phase at 0 minute: 66% MeOH/34% $H_2O$; at 60 minute: 100% MeOH/0% $H_2O$; at 76 minute: 100% MeOH/0% $H_2O$; at 78 minutes: 66% MeOH/34% $H_2O$; and at 86 minutes: 66% MeOH/34% $H_2O$; flow rate: 1.0 mL/min; and detection wavelength: 254 nm.

In other embodiments, the HC extract exhibits five peaks at retention times of (i) 24.45-29.59 minutes, (ii) 29.00-35.09 minutes, (iii) 39.36-47.63 minutes, (iv) 55.82-67.54 minutes, and (v) 63.73-77.11 minutes in a second performance liquid chromatography (HPLC) analysis using a linear gradient of acetonitrile (ACN) and water containing 0.1% trifluoroacetic acid (TFA), wherein the second HPLC analysis is carried out under the following condition: mobile phase at 0 minute: 10% ACN (in 0.05% TFA)/90% $H_2O$ (in 0.05% TFA); at 80 minutes: 17% ACN (in 0.05% TFA)/83% $H_2O$ (in 0.05% TFA); at 90 minutes: 100% ACN (in 0.05% TFA)/0% $H_2O$ (in 0.05% TFA); at 100 minutes: 100% ACN (in 0.05% TFA)/0% $H_2O$ (in 0.05% TFA); at 102 minute: 10% ACN (in 0.05% TFA)/90% $H_2O$ (in 0.05% TFA); and at 110 minute: 10% ACN (in 0.05% TFA)/90% $H_2O$ (in 0.05% TFA); flow rate: 1.0 mL/min; and detection wavelength: 254 nm.

In yet other embodiments, the HC extract exhibits four peaks at retention times of (i) 8.55-10.34 minutes, (ii) 17.64-21.34 minutes, (iii) 20.55-24.86 minutes, and (iv) 42.91-51.92 minutes in a first high performance liquid chromatography (HPLC) analysis using a linear gradient of methanol and water, and five peaks at retention times of (i) 24.45-29.59 minutes, (ii) 29.00-35.09 minutes, (iii) 39.36-47.63 minutes, (iv) 55.82-67.54 minutes, and (v) 63.73-77.11 minutes in a second performance liquid chromatography (HPLC) analysis using a linear gradient of acetonitrile (ACN) and water containing 0.1% trifluoroacetic acid (TFA), wherein the first HPLC analysis is carried out under the following condition: (1) mobile phase at 0 minute: 66% MeOH/34% $H_2O$; at 60 minute: 100% MeOH/0% $H_2O$; at 76 minute: 100% MeOH/0% $H_2O$; at 78 minutes: 66% MeOH/34% $H_2O$; and at 86 minutes: 66% MeOH/34% $H_2O$; flow rate: 1.0 mL/min; and detection wavelength: 254 nm; and the second HPLC analysis is carried out under the following condition: (2) mobile phase at 0 minute: 10% ACN (in 0.05% TFA)/90% $H_2O$ (in 0.05% TFA); at 80 minutes: 17% ACN (in 0.05% TFA)/83% $H_2O$ (in 0.05% TFA); at 90 minutes: 100% ACN (in 0.05% TFA)/0% $H_2O$ (in 0.05% TFA); at 100 minutes: 100% ACN (in 0.05% TFA)/0% $H_2O$ (in 0.05% TFA); at 102 minute: 10% ACN (in 0.05% TFA)/90% $H_2O$ (in 0.05% TFA); and at 110 minute: 10% ACN (in 0.05% TFA)/90% $H_2O$ (in 0.05% TFA); flow rate: 1.0 mL/min; and detection wavelength: 254 nm.

In still another aspect, the present disclosure provides a method for treating diabetes in a subject in need thereof, comprising administering to the subject an effective amount of any of the HC extracts described herein.

In some embodiments, the effective amount of the HC extract is sufficient to lower blood glucose levels, increase insulin levels, and/or reduce insulin resistance of the subject.

In other embodiments, the amount of the HC extract administered to a subject does not lower blood glucose levels of the subject in a fasting state.

Also within the scope of this disclosure is a pharmaceutical composition for use in treating diabetes, the pharmaceutical composition comprising an effective amount of any of the HC extracts as described herein and a pharmaceutically acceptable carrier.

The details of one or more embodiments of the invention are set forth in the description below. Other features or advantages of the present invention will be apparent from the following detailed description of several embodiments, and also from the appended claims.

BRIEF DESCRIPTION OF THE DRAWINGS

The foregoing summary, as well as the following detailed description of the invention, will be better understood when read in conjunction with the appended drawings. For the purpose of illustrating the invention, there are shown in the drawings embodiments which are presently preferred. It should be understood, however, that the invention is not limited to the precise arrangements and instrumentalities shown.

In the drawings.

DETAILED DESCRIPTION OF THE INVENTION

Figure 1:
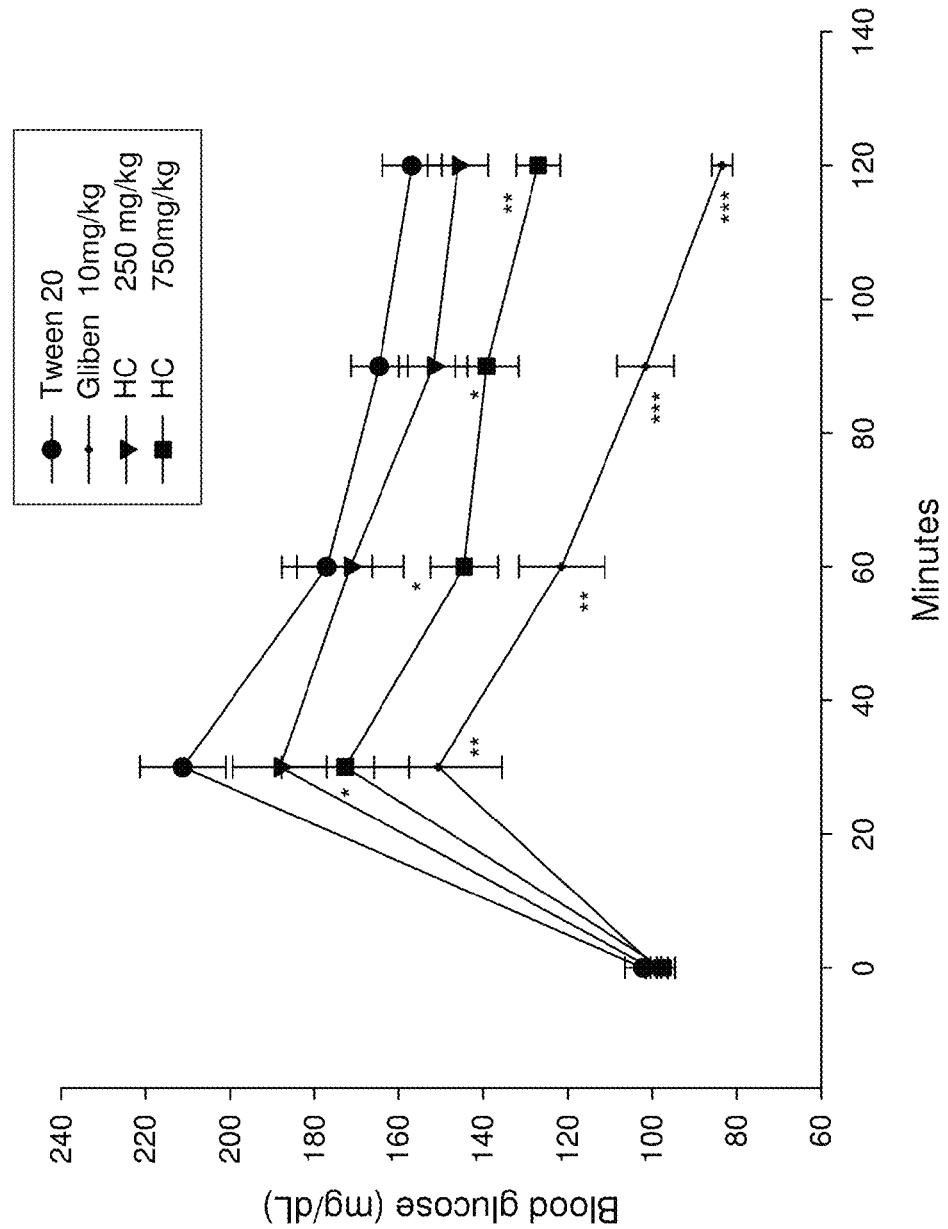
FIG. 1 illustrates the effect of the ethanol extract of leaves and pseudostems of *Hedychium coronarium Koenig* in reducing blood glucose in normal rats. "Control" represents oral administration of 10% Tween 20; "Gliben 10 mg/kg" represents oral administration of 10 mg/kg glibenclamide; "HC 250 mg/kg" represents oral administration of 250 mg/kg ethanol extract of leaves and pseudostems of *Hedychium coronarium Koenig*; and "HC 750 mg/kg" represents oral administration of 750 mg/kg ethanol extract of leaves and pseudostems of *Hedychium coronarium Koenig*. The X axis represents the time intervals of blood sampling, and the Y axis represents the concentration of blood glucose.

Unless defined otherwise, all technical and scientific terms used herein have the same meanings as is commonly understood by one of skill in the art to which this invention belongs.

As used herein, the articles "a" and "an" refer to one or more than one (i.e., at least one) of the grammatical object of the article. By way of example, "an element" means one element or more than one element.

"*Hedychium coronarium Koenig*" as used herein is an herbaceous perennial monocot plant (Family: Zingiberaceae, Order: Zingiberalesl Genus: *Hedychium*). The plant is native to India, Malaysia and Himalaya Mountains, and generally grows at lower elevations. In Taiwan, it can be found in mountain areas, fields, and gullies of Yilan, Taipei, Hsinchu, Taichung and Kaohsiung. The underground part includes rhizomes, which look like a ginger; and the overground part includes leaves and pseudostems formed by the leaf sheaths. The leaves are lance-shaped, 40 cm in long and 7 cm in wide, and smooth in the up sides and hairy in the down sides. Lips and petals are white and fragrant. *Hedychium coronarium Koening* reaches about 1-2 m in height and grows tufts, and makes great potted plants and cut flowers. The tender shoots and rhizomes are eatable. *Hedychium coronarium Koening* is also named as butterfly ginger, butterfly lily, ginger lily, ginger orchid, white butterfly lily, Gandasuli, and Kamia.

Diabetes is a disorder of sugar metabolism, including type I and type II. Type I diabetes, also known as juvenile onset diabetes or insulin-dependent diabetes, is characterized by the pancreas making too little or no insulin. Patients afflicted with type I diabetes depend on insulin for survival; without insulin, the patients develop sever metabolic complications, such as acute ketoacidosis and coma. Type II diabetes, also known as maturity onset diabetes or non-insulin-dependent diabetes, is characterized by excess glucose production in spite of the availability of insulin and high levels of circulating glucose levels as a result of inadequate glucose clearance, which is due to improper response to insulin, instead of insufficient levels of insulin.

The term "treating" as used herein refers to application or administration of a composition including one or more active agents to a subject, who has a disease, a symptom of the disease or a predisposition toward the disease, with the purpose to cure, heal, alleviate, relieve, alter, remedy, ameliorate, improve, or affect the disease, the symptom of the disease, or the predisposition toward the disease. For example, as used herein the term "treating diabetes" will refer in general to administration of an active agent to a subject in need thereof to reduce glucose levels, increase insulin levels, improve insulin sensitivity, reduce insulin resistance, and/or increase glucose consumption in the subject.

The term "subject" as used herein includes mammals, such as humans, companion animals (e.g., dogs, cats, and the like), farm animals (e.g., cows, sheep, pigs, horses, and the like) or laboratory animals (e.g., rats, mice, guinea pigs, and the like).

The term "effective amount" as used herein refers to that amount of an active agent or composition sufficient to achieve the above-described therapeutic efficacies in a subject. The effective amount may vary, for example, depending upon the types or dosage of the agent or composition and the weight, age and healthy condition of the subject to be treated.

The term "extract" as used herein refers to a product obtained by extraction of a substance. In general, an extract is a solution or concentrated preparation obtained by soaking or mixing a substance to be extracted with a solvent. Typically, an extract can be prepared from a fresh plant or a dried and/or powdered plant sample. There are various extraction processes known in the art, including but not limited to, maceration, percolation, repercolation, digestion, counter-current extraction, turbo-extraction, or carbon-dioxide hypercritical (temperature/pressure) extraction. Suitable solvents include but are not limited to water, ethanol, an ethanol/water mixture, methanol, butanol, iso-butanol, acetone, hexane, n-hexane, petroleum ether, ethyl acetate, dichloromethane, trichloromethane, or other organic solvents. One may select proper types of solvents or adjust their concentrations to achieve proper polarity so as to perform extraction as needed. According to the invention, low polarity solvents including but are not limited to petroleum ether, n-hexane, dichloromethane, trichloromethane, ethyl acetate, acetone, ethanol at a concentration of 70% or more (v/v in water); and high polarity solvents including but are not limited to water, ethanol at a concentration of 50% or less than 50% (v/v in water), methanol, butanol, iso-butanol, acetone at a concentration of 80% or less than 80% (v/v in water), are used to perform the extraction. The ratio of a substance to be extracted to a solvent can be about 1:1 to about 1:100 (w/v, g/ml), preferably about 1:1 to about 1:50 (w/v, g/ml), more preferably about 1:1 to about 1:20 (w/v, g/ml), even more preferably about 1:15 or about 1:10 (w/v, g/ml). Extraction may be conducted at a proper temperature, for example at a temperature from about 5° C. to about 100° C., from about 10° C. to about 100° C., from about 20° C. to about 100° C., from about 40° C. to about 100° C., from about 60° C. to about 100° C., preferably at a room temperature of about 25° C. or by boiling at 100° C. Products obtained from different steps of extraction may be combined. Additional steps may be further conducted, such as concentration, e.g. evaporation, purification or isolation, e.g. filtration, centrifugation, and chromatography, as needed. In one example, fresh plants or dried plant samples of the whole plants or parts thereof (optionally subjected to cutting or grinding), are mixed with or soaked in a proper solvent with stirring for a sufficient period of time, such as 4 hours or more, 6 hours or more, 8 hours or more, 10 hours or more, 12 hours or more, 14 hours or more, or 16 hours or more, at a room temperature or under heating; the solid debris (residues) are removed by filtration; the resultant liquid (supernatant or filtrate) is collected, where the soaking or mixing step may be repeated as needed and the resultant liquid (supernatant or filtrate) is optionally combined together; and the product can be further concentrated, purified or isolated.

The term "ethanol" or "alcohol" is used interchangeable herein. A percentage of ethanol or alcohol as used herein indicates the volume percentage of ethanol or alcohol in water. For example, 95% ethanol means a solution containing 95% ethanol and 5% water by volume (v/v). A percentage of other solvents as used herein also indicate the volume percentages of the solvents in water. For example, 80% acetone means a solution containing 80% acetone and 20% water by volume (v/v).

Preparation Processes of HC Extracts

The present invention provides novel preparation processes for preparing extracts from one or more overground parts of *Hedychium coronarium Koenig*. These processes produce HC extracts that exhibit unexpectedly high efficacies in treating diabetes.

As used herein, the plant, *Hedychium coronarium Koenig*, can be purchased from a local market or obtained from mountain areas in Taiwan. To conduct any of the preparation processes described herein, the overground part, typically including leaves and/or pseudostems, can be taken off from the plant, washed with water, air dried, and subjected to cutting or grinding to powder (through a 20-30 mesh sieve). The dried powder samples can be extracted by mixing or soaking with a suitable amount of a low polarity solvent, e.g., ethanol at a concentration of at least 70% (v/v in water) (e.g., 80%, 90%, or 95%).

Low polarity solvents are well known in the art. Examples include, but are not limited to, petroleum ether, n-hexane, dichloromethane, trichloromethane, ethyl acetate, acetone, ethanol at a concentration of 70-100% (v/v in water).

Particularly, to conduct the extraction step with the low polarity solvent, the overground part of *Hedychium coronarium Koening* and the low polarity solvent can be present in a ratio of about 1:1 to about 1:100 (w/v, g/ml), preferably about 1:1 to about 1:50 (w/v, g/ml), more preferably about 1:1 to about 1:20 (w/v, g/ml), even more preferably about 1:15 or about 1:10 (w/v, g/ml). Extraction can be conducted at a proper temperature, for example, at a temperature from about 5° C. to about 100° C., from about 10° C. to about 100° C., from about 20° C. to about 100° C., from about 40° C. to about 100° C., from about 60° C. to about 100° C., preferably at a room temperature of about 25° C. or by boiling at 100° C., for a sufficient period of time, such as 4 hours or more, 6 hours or more, 8 hours or more, 10 hours or more, 12 hours or more, 14 hours or more, or 16 hours or more. In one certain example, the overground part of *Hedychium coronarium Koening* is soaked in about 10 fold volume of 95% ethanol with stirring at room temperature for about 16 hours. After extraction, filtration is conducted and the filtrate is collected. The solid residues thus produced can be again soaked in the low polarity solvent to repeat the extraction. The filtrate thus obtained can be combined together and harvested. The filtrate as collected can be optionally concentrated (for example under reduced pressure) to a volume of about 0.1-1.0% (particularly about 0.5%) of the volume before concentration (the "first extract").

Preparation Process I

In preparation process I, an overground part of *Hedychium coronarium Koenig* is extracted with a low polarity solvent as described above and the extract thus obtained is then subjected to ion exchange chromatography.

Ion exchange chromatography is a chromatographic process in which an ionizable components of interest interacts with an oppositely charged ligand linked to a solid phase ion exchange material under appropriate conditions of pH and conductivity, such that the components of interest interacts non-specifically with the charged compound more or less than the undesired components in the mixture. The undesired components in the mixture can be washed from a column of the ion exchange material or are bound to or excluded from the resin, faster or slower than the solute of interest. Suitable ion exchange column as used herein includes a macroporous resin column. The ion exchange resin preferably is a suspension polymerized polymer having a polystyrene or divinylbenzene skeleton, which can form a pore size around 100-2000 nm. Commercially available examples of the ion exchange column include Diaion HP20 Diaion® HP-10, -20, -30, -40, -50 (Mitsubishi Chemicals K.K.); Amberlite XAD-4, -6, -1180, -1600 (Rohm and Hass Company); XAD-4, XAD-7, XAD-16, 1-0377, 1-0393, and 1-0379 (Sigma-Aldrich).

To conduct the ion exchange chromatography, the first extract as described herein is loaded to a first ion exchange chromatography column, and then elution is performed by passing through (washing) the first ion exchange chromatography column a solution of water and ethanol at a volume ratio from 1:1 to 1:9, and then eluting the ion exchange chromatography column with ethanol at a concentration of at least 70% (v/v in water) (e.g., at least 80%, at least 90%, or at least 95%), to produce an eluate, which can be collected as the HC extract from Preparation Process I. In one embodiment, the first extract, prior to ion exchange chromatography, is diluted with a proper solvent, such as a mixture of 95% ethanol and water (8:2). In a certain example, the first extract, after proper dilution, is loaded onto a macroporous resin column (e.g. a DIAION column HP20), which can be pre-treated by ethanol. In another example, a solution of water and ethanol at a volume ratio of 2:8 (i.e. 1:4) is used to wash the column that is loaded with the extract. The column can then be eluted with 95% ethanol to produce the HC extract. See Example 13.

Preparation Process II

In preparation process II, the plant can be first extracted with a low polarity solvent and filtrated as described above. The solid residues resulting from the extracting process can be harvested and extracted with a high polarity solvent. The resultant extract (the second extract) can then be subjected to ion exchange chromatography.

High polarity solvents are also well known in the art. Examples include, but are not limited to, water, ethanol at a concentration of up to 50% (v/v in water) (e.g., 5-50%, 10-50%, 20-50%, or 30-50%), methanol, butanol, iso-butanol, acetone at a concentration of up to 80% (v/v in water) (e.g., 5-80%, 10-80%, 20-80%, 30-80%, or 40-80%), or any combinations thereof. One certain example of the high polarity solvent as used herein is 50% ethanol (v/v in water).

To conduct the extraction step with a high polarity solvent, the solid residues (produced from the extraction with a low polarity solvent in the preparation process I) and the high polarity solvent can be present in a ratio of about 1:1 to about 1:100 (w/v, g/ml), preferably about 1:1 to about 1:50 (w/v, g/ml), more preferably about 1:1 to about 1:20 (w/v, g/ml), even more preferably about 1:15 or about 1:10 (w/v, g/ml). The extraction can be conducted at a proper temperature for a sufficient period of time as described above. In one certain example, the solid residues are soaked in about 15 fold volume of 50% ethanol with stirring at room temperature for about 16 hours. After extraction, filtration is conducted and the filtrate is collected. The solid residues thus produced can be again soaked in the high polarity solvent to repeat the extraction. The filtrate thus obtained can be combined together and harvested. The filtrate as collected can be optionally concentrated (for example under reduced pressure) to a volume of about 0.1-1.0%, preferably 0.5% of the volume before concentration. The second extract as obtained is then subjected to ion exchange chromatography for isolation as described herein.

To conduct the ion exchange chromatography, the second extract is loaded onto a second ion exchange chromatography column. Elution can be performed by first passing through (washing) the second ion exchange chromatography column with water and then eluting the column with ethanol at a concentration of 5-50% (v/v in water) (e.g., 10-50%, 20-50%, 30-50%, or 40-50%) to produce an eluate, which can be collected as an HC extract prepared from Preparation Process II. Suitable ion exchange columns are well known in the art and also described herein. In one embodiment, the second extract, prior to ion exchange chromatography, is diluted with a proper aqueous solution. In one certain example, the second extract, after proper dilution, is loaded to a macroporous resin column (e.g. a DIAION column HP20), which has been pre-treated by ethanol. After being washed with water, the column is eluted with about 30% ethanol to produce the HC extract. See Example 15.

Preparation Process III

The HC extract produced in Preparation process I and the extract prepared by Preparation process II can be mixed to produce a combined HC extract. See Example 16.

Analysis of the Components in the HC Extracts

The HC extracts obtained as described herein can then be analyzed by high-performance liquid chromatography (HPLC) to characterize the components contained therein.

In one example, the HC extract obtained from the preparation process I (i.e. the first isolated fluid) exhibits four major peaks at retention times of (i) 8.55-10.34, (ii) 17.64-21.34, (iii) 20.55-24.86 and (iv) 42.91-51.92 in a HPLC analysis using a linear gradient of methanol and water. Specifically, the four major peaks are shown at retention times of about 9.4, about 19.4, about 22.6 and about 47.2 minutes. The HC extract further exhibits three minor peaks at retention times of (i) 29.91-36.20, (ii) 33.45-40.48, and (iii) 54.09-65.45 in the same condition. Specifically, the three minor peaks are shown at retention time of about 32.9, about 36.8 and about 59.5. In one example, the HPLC analysis is carried under the following condition: (1) mobile phase at 0 minute: 66% MeOH/34% $H_2O$; at 60 minute: 100% MeOH/0% $H_2O$; at 76 minute: 100% MeOH/0% $H_2O$; at 78 minutes: 66% MeOH/34% $H_2O$; and at 86 minutes: 66% MeOH/34% $H_2O$; flow rate: 1.0 mL/min; and detection wavelength: 254 nm. See example 18 and FIG. 11(A).

In another example, the HC extract obtained from the preparation process II (i.e. the second isolated fluid) exhibits five peaks at retention times of (i) 24.45-29.59, (ii) 29.00-35.09, (iii) 39.36-47.63, (iv) 55.82-67.54 and (v) 63.73-77.11 in a HPLC analysis using a linear gradient of acetonitrile (ACN) and water containing 0.1% trifluoroacetic acid (TFA). Specifically, the five peaks are shown at retention times of about of 26.9, about 31.9, about 43.3, about 61.4 and about 70.1. In one example, the HPLC analysis is carried under the following condition: mobile phase at 0 minute: 10% ACN (0.05% TFA)/90% $H_2O$ (0.05% TFA); at 80 minutes: 17% ACN (0.05% TFA)/83% $H_2O$ (0.05% TFA); at 90 minutes: 100% ACN (0.05% TFA)/0% $H_2O$ (in 0.05% TFA); at 100 minutes: 100% ACN (in 0.05% TFA)/0% $H_2O$ (in 0.05% TFA); at 102 minute: 10% ACN (in 0.05% TFA)/90% $H_2O$ (in 0.05% TFA); and at 110 minute: 10% ACN (in 0.05% TFA)/90% $H_2O$ (in 0.05% TFA); flow rate: 1.0 mL/min; and detection wavelength: 254 nm. See example 18 and FIG. 11(B).

In a further example, the HC extract obtained from the preparation process III (i.e. the combined product) exhibits four peaks at retention times of (i) 8.55-10.34, (ii) 17.64-21.34, (iii) 20.55-24.86 and (iv) 42.91-51.92 minutes in a HPLC analysis using a linear gradient of methanol and water, and five peaks at retention times of (i) 24.45-29.59, (ii) 29.00-35.09, (iii) 39.36-47.63, (iv) 55.82-67.54 and (v) 63.73-77.11 minutes in a HPLC analysis using a linear gradient of acetonitrile (ACN) and water containing 0.1% trifluoroacetic acid (TFA). The HPLC conditions are as described above. See Example 18 and FIG. 11(C).

Pharmaceutical Compositions Comprising the HC Extracts and Uses Thereof in Treating Diabetes The HC extracts prepared according to the invention have the efficacies of lowering blood glucose levels, increasing insulin levels and/or reducing insulin resistance, and therefore can be used for treating diabetes. Specifically, the HC extracts of the invention are glucose-dependent, which therefore will not overly reduce blood glucose in a subject, such as in a fasting subject, and thus may prevent hypoglycermia (one of the side effects resulted from conventional anti-diabetes medicaments). These efficacies of the HC extracts of the invention can be assessed by standard approaches or methods known in the art, including, but not limited to, a fasting glucose test, glucose tolerance test, insulin increasing test and insulin resistance test.

In healthy individuals, blood levels can be maintained normally by an effective glucose regulating mechanism. However, hypoglycemia is generally found in diabetic patients receiving insulin or other pharmacological treatment. The mean normal blood glucose level in human is about 70-130 mg/dL before meals and no more than about 180 mg/dL after meals. In this connection, 60-70 mg/dL is commonly used as the lower limit of normal glucose level. A fasting state, which may mean that a subject has not eaten for 8 hours or more, particularly 12 hours or more, and more particularly 16 hours or more, may cause a relatively low glucose level. Symptoms of hypoglycemia may occur until the blood level drops to 50 mg/dL. One of the valuable advantages of the HC extracts of the invention is that they are glucose-dependent, which means that they would not make the sugar level drop when the patient's blood sugar is normal or at a low level (such as at a fasting state), and thus can prevent hypoglycemia. The glucose dependent property of the HC extracts of the invention can be determined by an intraperitoneal glucose tolerance test (IPGTT) in normal animals, for example. In IPGTT, it was found that the blood glucose level in normal mice receiving the HC extracts of the invention at 90 minute was similar to that at 0 minutes, indicating that the extracts of the invention will not overly reduce blood glucose in a subject, which means that the extracts of the invention has the potential to control the blood glucose level without the risk of hypoglycemia.

Insulin resistance as used herein describes a condition in which physiological amounts of insulin are inadequate to produce a normal insulin response from cells or tissues, which may occur when insulin levels are high over a prolonged period of time that causes the body's sensitivity to the hormone to be reduced. The HC extract of the invention can reduce insulin resistance and cause the blood glucose levels to be effectively regulated by insulin.

Accordingly, the present invention provides a method for treating diabetes in a subject in need thereof, comprising administering to the subject an effective amount of the HC extract of the invention. The diabetes includes type I and type II diabetes. Specifically, the effective amount of the HC extract is sufficient to lower blood glucose levels, increasing insulin levels, and/or reduce insulin resistance of the subject. More specifically, the effective amount of the HC extract does not overly reduce blood glucose levels of the subject, especially when he/she is in a fasting state, and thus can prevent hypoglycemia.

To perform the above-noted treatment and facilitate delivery, the HC extract of the invention can be formulated with a pharmaceutically acceptable carrier to form a pharmaceutical composition.

The term "pharmaceutically acceptable" as used herein means the carrier is compatible with the active ingredient contained in the composition, preferably capable of stabilizing the active ingredient, and not deleterious to the subject to be treated.

The carrier may serve as a diluent, vehicle, excipient, or medium for the active ingredient. Some examples of suitable excipients include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, sterile water, syrup, and methyl cellulose. The composition can additionally include lubricating agents such as talc, magnesium stearate, and mineral oil; wetting agents; emulsifying and suspending agents; preserving agents such as methyl- and propylhydroxy-benzoates; sweetening agents; and flavoring agents. The composition of the invention can be formulated by a procedure known in the art to provide fast, sustained or delayed release of the active ingredient. Depending on the mode of administration, the pharmaceutical composition of the invention contain 0.1 to 100% of the active ingredient, more specifically, 1 to 100% of the active ingredient, even more specifically, 5 to 50% of the active ingredient, by weight on the basis of the total weight of the composition.

The compositions of the invention can be in any forms as desired, including but not limited to, tablets, pills, powders, lozenges, sachets, cachets, suppositories, suspensions, emulsions, solutions, syrups, soft and hard gelatin capsules, sterile injectable solutions, packaged powders, mist, implants or patches. In a particular embodiment, the composition of the invention is in the form of tablets. The composition of the invention can be delivered through any medically acceptable route, such as orally, parentally e.g. intramuscularly, intravenously, subcutaneously, interperitoneally, transdermally, by rectum or inhalation, or vaginal, ocular or nasal routes. In a certain embodiment, the composition of the invention is orally administered to a subject in need.

A subject in need of the treatment described herein can be a human patient having, suspected of having, or at risk for diabetes (either Type I or Type II). A subject suspected of having diabetes might show one or more symptoms of the disease, e.g., blurry vision, excess thirst, fatigue, frequent urination, hunger, or weight loss. A subject who is at risk for diabetes may bear one or more risk factors associated with this disease. Risk factors for Type I diabetes include, but are not limited to, genetics and family history, pancreatic diseases, and infection. Risk factors for Type II diabetes include, but are not limited to, obesity or being overweight, age (over 45), family history of diabetes, HDL cholesterol level (e.g., under 35 mg/dL), high blood pressure, high blood level of triglycerides (250 mg/dL or more), impaired glucose tolerance, and low activity level.

Without further elaboration, it is believed that the above description has adequately enabled the present invention. The following examples are, therefore, to be construed as merely illustrative, and not limitative of the remainder of the disclosure in any way whatsoever. Specifically, US Patent Publication No. 2011/0195139 is hereby incorporated by reference in its entirety.

EXAMPLES

Example 1

Glucose Tolerance Test of Ethanol Extract of Leaves and Pseudostems of Hedychium coronarium Koening in Normal Rats Twenty-six (26) Sprague-Dawley rats were divided into four groups: the placebo group (7 rats, to be administered with 10% Tween 20), the positive control group (7 rats, to be administered with glibenclamide), the 250 mg/kg HC group (6 rats, to be administered with 250 mg/kg ethanol extract of leaves and pseudostems of Hedychium coronarium Koening), and the 750 mg/kg HC group (6 rats, to be administered with 750 mg/kg ethanol extract of the leaves and pseudostems of Hedychium coronarium Koening). The rats were fasted for 7 hours and then administered with 250 mg/kg ethanol extract of leaves and pseudostems of Hedychium coronarium Koening (the 250 mg/kg HC group), 750 mg/kg ethanol extract of leaves and pseudostems of Hedychium coronarium Koening (the 750 mg/kg HC group), 10 mg/kg glibenclamide (the positive control group), or 10% Tween 20 (the placebo/control group). After 30 minutes, each rat was administered with glucose at a total amount of 5 g/kg, orally (2.5 g/kg) and subcutaneously (2.5 g/kg). Blood was drawn from each rat at the intervals of 0, 30, 60, 90 and 120 minutes for the measurement of glucose (mg/DL). The results are shown in the table below and FIG. 1.

| | Concentration of blood glucose (mg/DL) | | | | |
|---|---|---|---|---|---|
| Group | 0 min | 30 min | 60 min | 90 min | 120 min |
| Placebo group | 102.1 +/− 4.2 | 211.1 +/− 10.2 | 177 +/− 10.7 | 164.6 +/− 6.7 | 156.9 +/− 7.0 |
| Glibenclamide group | 99 +/− 2.7 | 150.7 +/− 15.2** | 121.4 +/− 10.2** | 101.6 +/− 6.7** | 83.4 +/− 2.5*** |
| 250 mg/kg HC group | 100.2 +/− 1.3 | 188.2 +/− 11.1 | 171.5 +/− 12.6 | 151.8 +/− 8.1 | 146 +/− 7.2 |
| 750 mg/kg HC group | 97.5 +/− 2.8 | 172.7 +/− 15.1* | 144.5 +/− 8.0* | 139.2 +/− 7.5* | 127 +/− 5.2** |

The data is expressed with mean +/− standard error (SEM). P values are calculated by t-test of Sigma Statistical Software, wherein $p < 0.05$ is considered significant and marked with the symbol "*";
$p < 0.01$ is considered highly significant and marked with the symbol "**"; and
$p \leq 0.001$ is considered very highly significant and marked with the symbol "***".

The results show that when compared with the control group, the blood glucose levels at intervals of 30, 60 and 90 minutes after administration of glucose were significantly reduced and that at interval of 120 minutes after administration of glucose were highly significantly reduced, in the 750 mg/kg HC group.

Example 2

Glucose Tolerance Test of Ethanol Extract of Leaves and Pseudostems of *Hedychium coronarium Koening* in Mice with Type II Diabetes (Short-Term Postprandial Blood Glucose)

Figure 2:
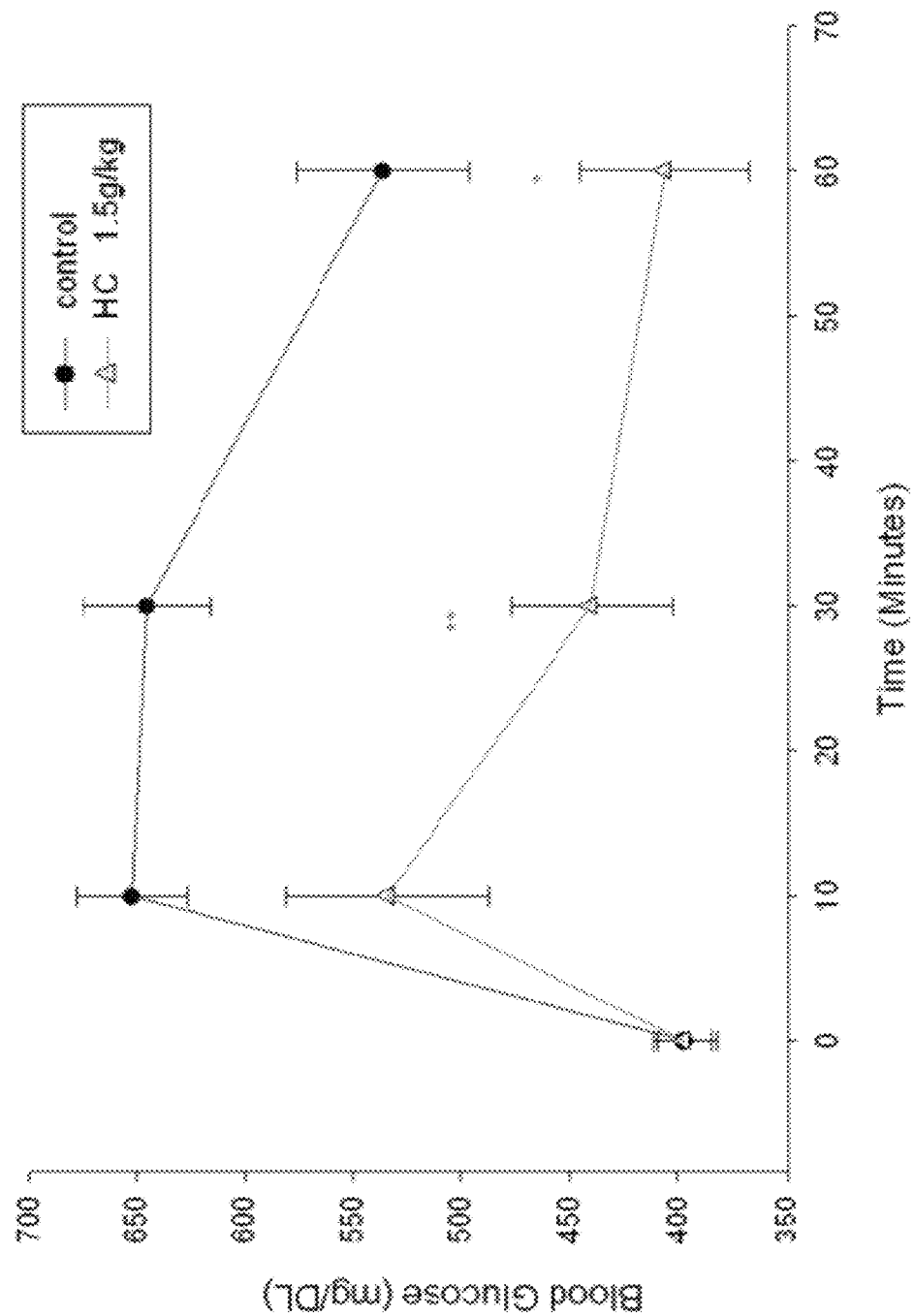
FIG. 2 illustrates the effect of the ethanol extract of leaves and pseudostems of *Hedychium coronarium Koenig* in reducing blood glucose in $db^+/db^+$ mice with type II diabetes in the glucose tolerance test. "Control" represents oral administration of 10% Tween 20; and "HC 1.5 g/kg" represents oral administration of 1.5 g/kg ethanol extract of leaves and pseudostems of *Hedychium coronarium Koenig*. The X axis represents the time intervals of measurement of blood sampling, and the Y axis represents the concentration of blood glucose. P values are calculated by t-test of Sigma Statistical Software wherein $p<0.05$ is considered significant and marked with *; $p<0.01$ is considered highly significant and marked with ; and $p \leq 0.001$ is considered very highly significant and marked with *.

Twelve (12) mice with type II diabetes ($db^+/db^+$ mice) were fasted for 12 hours and then allowed to feed freely for two hours. Subsequently, 6 mice of the control group were orally administered with 10% Tween 20, and 6 mice of the 1.5 g/kg HC group were orally administered with 1.5 g/kg ethanol extract of leaves and pseudostems of *Hedychium coronarium Koening*. Blood was drawn from each animal at intervals of 0, 10, 30 and 60 minutes after administration for measurement of glucose (mg/DL). The results are shown in the table below and FIG. 2.

| | Concentration of blood glucose (mg/DL) | | | |
|---|---|---|---|---|
| Group | 0 min | 10 min | 30 min | 60 min |
| Control group; N = 6 | 397.0 ± 12.6 | 652.2 ± 25.5 | 645 ± 29.8 | 536.3 ± 40.3 |
| HC group; N = 6 | 396.8 ± 15.1 | 534.3 ± 47.0 | 440.2 ± 37.2** | 406.5 ± 38.8* |

The data is expressed with mean +/− standard error (SEM). P values are calculated by t-test of Sigma Statistical Software, wherein $p < 0.05$ is considered significant and marked with the symbol "*";
$p < 0.01$ is considered highly significant and marked with the symbol "**"; and
$p \leq 0.001$ is considered very highly significant and marked with the symbol "***".

The results show that when compared with the control group, the blood glucose levels at interval of 30 minutes after administration of glucose were highly significantly reduced and that at interval of 60 minutes after administration of glucose were significantly reduced, in the 1.5 g/kg HC group.

Example 3

Figure 3:
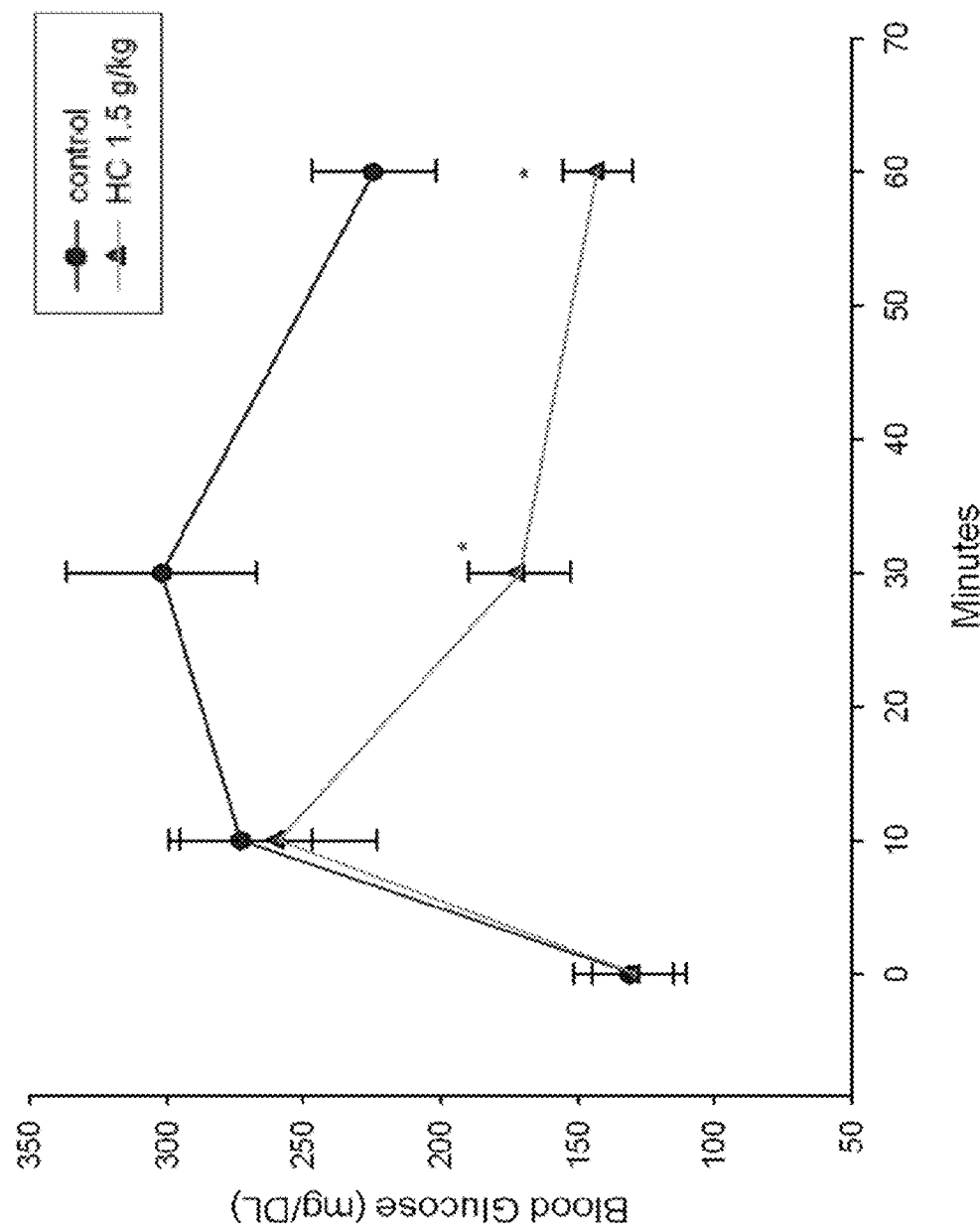
FIG. 3 illustrates the effect of the ethanol extract of leaves and pseudostems of *Hedychium coronarium Koenig* in reducing blood glucose in normal $db^-/db^-$ mice in the intraperitoneal glucose tolerance test. "Control" represents oral administration of 10% Tween 20; and "HC 1.5 g/kg" represents oral administration of 1.5 g/kg ethanol extract of leaves and pseudostems of *Hedychium coronarium Koenig*. The X axis represents the time intervals of blood sampling, and the Y axis represents the concentration of blood.

Intraperitoneal Glucose Tolerance Test of Ethanol Extract of Leaves and Pseudostems of *Hedychium coronarium Koening* in Normal Mice Eight (8) mice ($db^-/db^-$ mice) were divided into two groups: the control group (4 mice, to be administered with 10% Tween 20) and the 1.5 g/kg HC group (4 mice, to be administered with 1.5 g/kg ethanol extract of leaves and pseudostems of *Hedychium coronarium Koening*). The mice were fasted for 14 hours and then allowed to feed freely for two hours. Subsequently, these animals were orally administered with 10% Tween 20 (the control group) or 1.5 g/kg ethanol extract of leaves and pseudostems of *Hedychium coronarium Koening* (the 1.5 g/kg HC group). After 30 minutes, each mouse was intraperitoneally administered with 1.5 g/kg glucose. Blood was drawn from each animal at intervals of 0 minutes, 10 minutes, 30 minutes and 60 minutes for the measurement of glucose (mg/DL). The results are shown in the table below and FIG. 3.

| | Concentration of blood glucose (mg/DL) | | | |
|---|---|---|---|---|
| Group | 0 min | 10 min | 30 min | 60 min |
| Control group | 130.8 +/− 20.7 | 273 +/− 26.5 | 301.8 +/− 34.8 | 224.3 +/− 22.6 |
| 1.5 g/kg HC group | 129.5 +/− 14.9 | 259.3 +/− 35.9 | 171.3 +/− 18.6* | 142.8 +/− 12.7* |

The data is expressed with mean +/− standard error (SEM). P values are calculated by t-test of Sigma Statistical Software, wherein $p < 0.05$ is considered significant and marked with the symbol "*";
$p < 0.01$ is considered highly significant and marked with the symbol "**"; and
$p \leq 0.001$ is considered very highly significant and marked with the symbol "***."

The results show that when compared with the control group, the blood glucose levels at intervals of 30 and 60 minutes after administration of glucose were significantly reduced in the 1.5 g/kg HC group. It demonstrates that the blood glucose in normal mice can be significantly reduced by the HC extract.

Example 4

Figure 4:
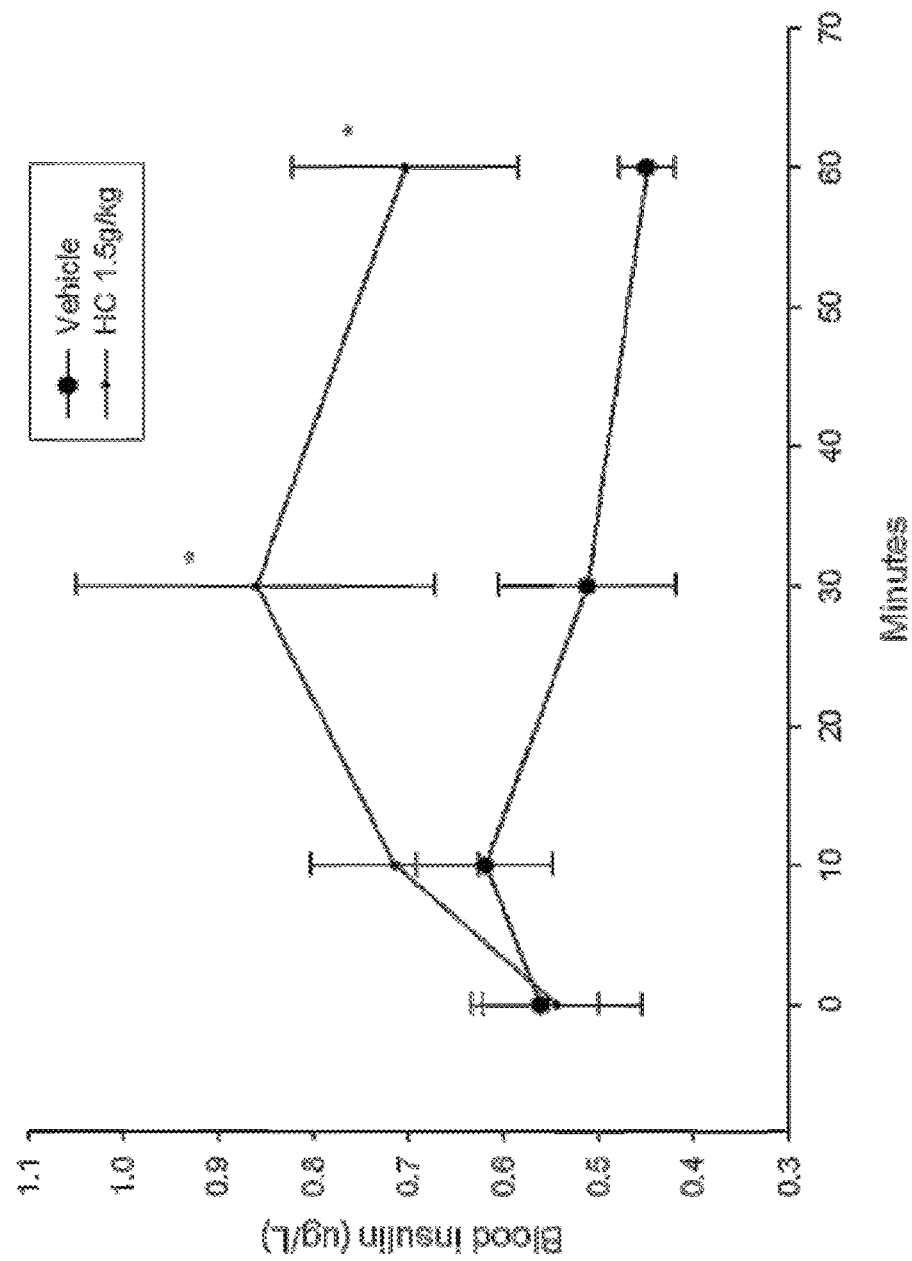
FIG. 4 illustrates the effect of the ethanol extract of leaves and pseudostems of *Hedychium coronarium Koenig* in promoting insulin secretion in normal $db^-/db^-$ mice in the intraperitoneal glucose tolerance test. "Control" represents oral administration of 10% Tween 20; and "HC 1.5 g/kg" represents oral administration of 1.5 g/kg ethanol extract of leaves and pseudostems of *Hedychium coronarium Koenig*. The X axis represents the time intervals of blood sampling, and the Y axis represents the concentration of blood insulin.

Insulin Increasing Test of Ethanol Extract of Leaves and Pseudostems of *Hedychium coronarium Koening* in Normal Mice The test mice and procedures were as described in Example 3. Blood was drawn from each animal at intervals of 0, 10, 30 and 60 minutes for the measurement of insulin (μg/L). The results are shown in the table below and FIG. 4.

| | Concentration of insulin (μg/L) | | | |
|---|---|---|---|---|
| Group | 0 min | 10 min | 30 min | 60 min |
| Control group | 0.56 +/− 0.04 | 0.62 +/− 0.05 | 0.51 +/− 0.07 | 0.45 +/− 0.02 |
| 1.5 g/kg HC group | 0.54 +/− 0.06 | 0.71 +/− 0.06 | 0.86 +/− 0.13* | 0.70 +/− 0.08* |

The data is expressed with mean +/− standard error (SEM). P values are calculated by t-test of Sigma Statistical Software, wherein $p < 0.05$ is considered significant and marked with the symbol "*";
$p < 0.01$ is considered highly significant and marked with the symbol "**"; and
$p \leq 0.001$ is considered very highly significant and marked with the symbol "***".

The results show that when compared with the control group, the insulin concentrations at intervals of 30 and 60 minutes after administration of glucose were significantly increased in the 1.5 g/kg HC group. It demonstrates that the ethanol extract of the leaves and pseudostems of *Hedychium coronarium Koening* significantly promotes the secretion of insulin.

Example 5

Figure 5:
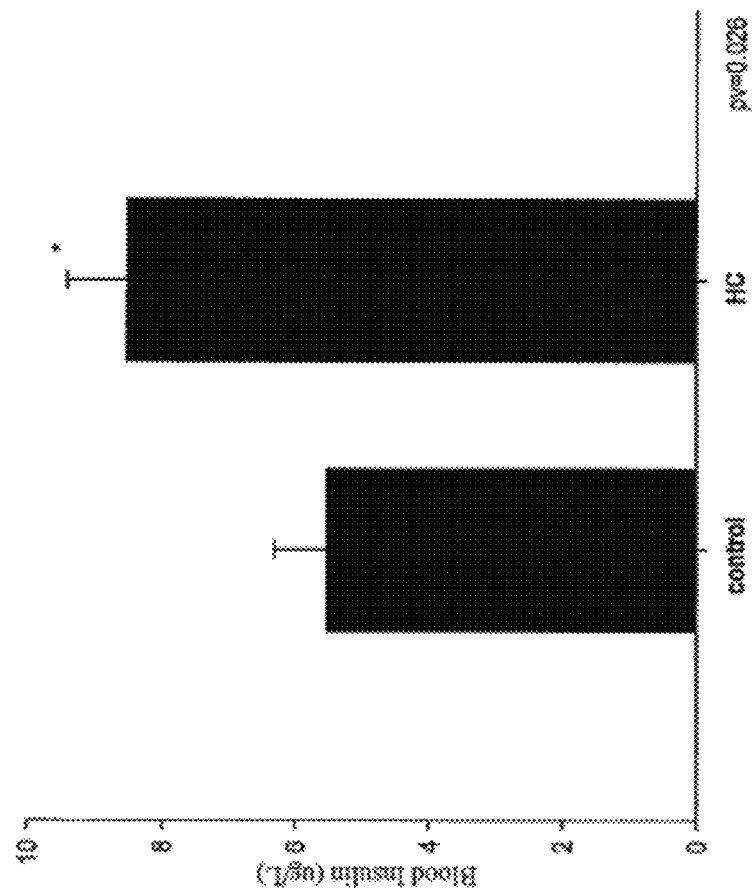
FIG. 5 illustrates the effect of the ethanol extract of leaves and pseudostems of *Hedychium coronarium Koenig* in promoting insulin secretion in $db^+/db^+$ mice with type II diabetes in the glucose tolerance test. "Control" represents oral administration of 10% Tween 20; and "HC" represents oral administration of 1.5 g/kg ethanol extract of leaves and pseudostems of *Hedychium coronarium Koenig*. The X axis represents the time intervals of blood sampling, and the Y axis represents the concentration of blood insulin.

Insulin Increasing Test of Ethanol Extract of Leaves and Pseudostems of *Hedychium coronarium Koening* in Mice with Type II Diabetes The test mice and procedures were as described in Example 2. Blood was drawn from each animal at 60 minutes for the measurement of insulin (μg/L). The results are shown in FIG. 5. The concentrations of insulin in the 1.5 g/kg HC group and control groups were 8.51+/−0.88 μg/L and 5.51+/−0.79 μg/L. These results show that ethanol extract of leaves and pseudostems of *Hedychium coronarium Koening* significantly promotes the secretion of insulin in mice with type II diabetes.

Example 6

Figure 6:
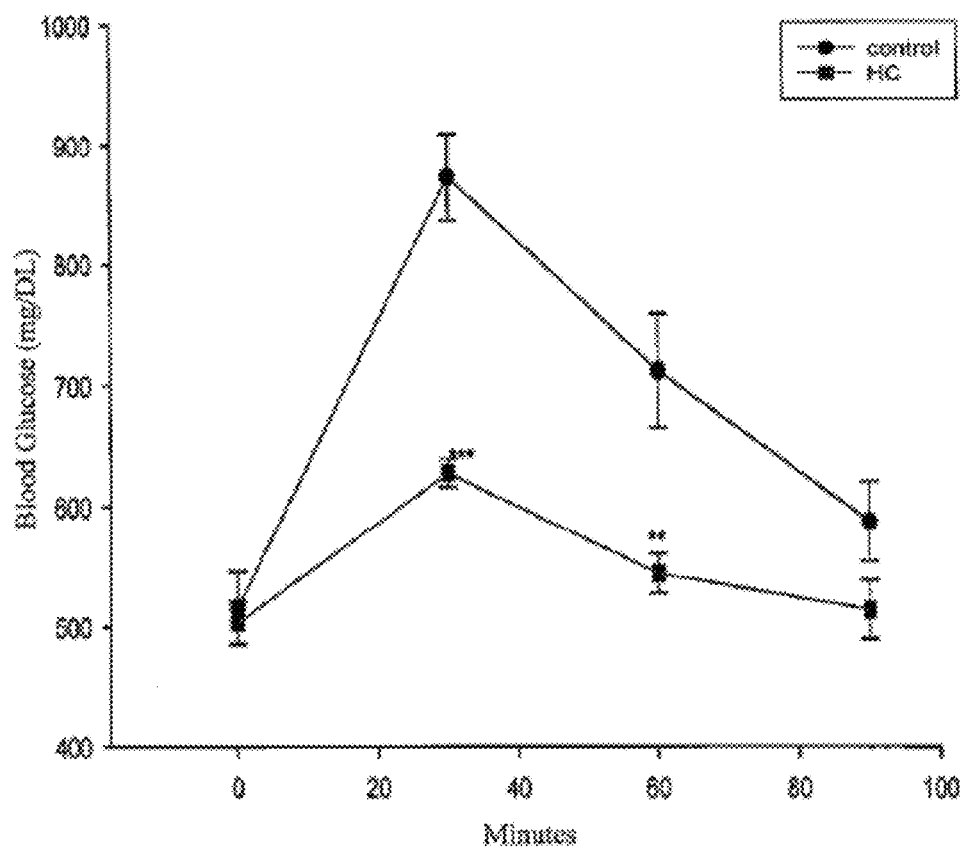
FIG. 6 illustrates the effect of the ethanol extract of leaves and pseudostems of *Hedychium coronarium Koenig* in reducing blood glucose in rats with type I diabetes in the glucose tolerance test. "Control" represents oral administration of 10% Tween 20 and subcutaneous administration of normal saline, and "HC" represents oral administration of 1 g/kg ethanol extract of leaves and pseudostems of *Hedychium coronarium Koenig*. The X axis represents the time intervals of blood sampling, and the Y axis represents the concentration of blood glucose.

Glucose Tolerance Test of Leaves and Pseudostems of Ethanol Extract of *Hedychium coronarium Koening* in Rats with Type I Diabetes Twelve (12) Sprague-Dawley rats with type I diabetes were divided into two groups: the control group (6 rats, to be administered with 10% Tween 20) and the 1 g/kg HC group (6 rats, to be administered with 1 g/kg ethanol extract of leaves and pseudostems of *Hedychium coronarium Koening* ). The rats were fasted for 4 hours and then orally administered with 10% Tween 20 (the control group) or 1 g/Kg ethanol extract of leaves and pseudostems of *Hedychium coronarium Koening* (the 1 g/kg HC group). After 30 minutes, each rat was administered with 2.5 g/kg glucose. Blood was drawn from each animal at intervals of 0 minutes, 30 minutes, 60 minutes, and 90 minutes for the measurement of glucose (mg/DL). The results are shown in the table below and FIG. 6.

| | Concentration of blood glucose (mg/DL) | | | |
|---|---|---|---|---|
| Group | 0 min | 30 min | 60 min | 90 min |
| Control group | 515.7 +/− 30.6 | 873 +/− 36.2 | 711.7 +/− 47.0 | 587.3 +/− 33.2 |
| 1 g/kg HC group | 503.5 +/− 17.8 | 627.8 +/− 11.3*** | 544 +/− 16.5** | 513.8 +/− 24.4 |

The data is expressed with mean +/− standard error (SEM). P values are calculated by t-test of Sigma Statistical Software, wherein $p < 0.05$ is considered significant and marked with the symbol "*";
$p < 0.01$ is considered highly significant and marked with the symbol "**"; and
$p \leq 0.001$ is considered very highly significant and marked with the symbol "***".

The results show that when compared with the control group, the blood glucose levels at intervals of 30 and 60 minutes after administration of glucose were significantly reduced in the 1 g/kg HC group. It demonstrates that the ethanol extract of leaves and pseudostems of *Hedychium coronarium* has an beneficial effect in reducing blood glucose in type I diabetes rats.

Example 7

Figure 7:
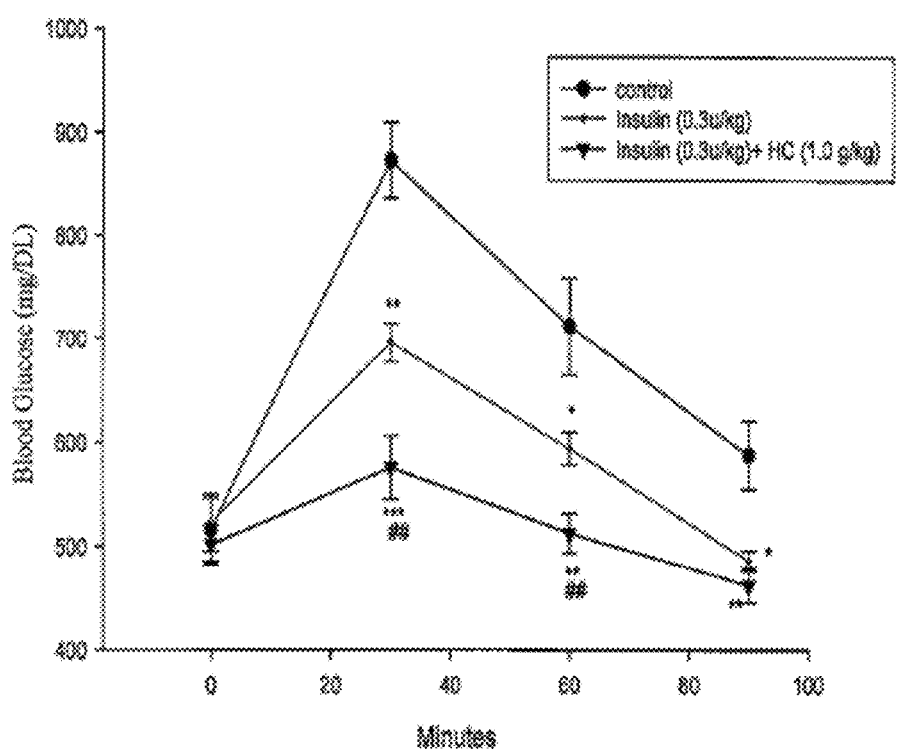
FIG. 7 illustrates the effect of the ethanol extract of leaves and pseudostems of *Hedychium coronarium Koenig* in insulin resistance in rats with type I diabetes in the glucose tolerance test. "Control" represents oral administration of 10% Tween 20 and subcutaneous administration of normal saline; "insulin (0.3 U/kg)" represents oral administration of 10% Tween 20 and subcutaneous administration of 0.3 U/kg insulin; and "insulin (0.3 U/kg)+HC (1.0 g/kg)" represents oral administration of 1 g/kg ethanol extract of leaves and pseudostems of *Hedychium coronarium Koenig* and subcutaneous administration of 0.3 U/kg insulin. The X axis represents the time intervals of blood sampling, and the Y axis represents the concentration of blood glucose.

Insulin Resistance Test of Ethanol Extract of Leaves and Pseudostems of *Hedychium coronarium Koening* in Rats with Type I Diabetes Eighteen (18) Sprague-Dawley rats with type I diabetes were divided into three groups: the control group (6 rats, to be administered with 10% Tween 20), the insulin group (6 rats, to be subcutaneously administered with 0.3 U/kg insulin) and the insulin plus HC group (6 rats, to be subcutaneously administered with 0.3 U/kg insulin and orally administered with 1.0 g/kg of ethanol extract of leaves and pseudostems of *Hedychium coronarium Koening* ). The rats were fasted for 4 hours and then administered with 10% Tween 20 (the control group), 0.3 U/kg insulin (the insulin group) or 0.3 U/kg insulin plus 1.0 g/Kg of ethanol extract of leaves and pseudostems of *Hedychium coronarium Koening* (the insulin plus HC group). After administration of 2.5 g/kg glucose, blood was drawn from each animal at 30-minute intervals for the measurement of glucose (mg/DL). The results are shown in the table below and FIG. 7.

| | Concentration of blood glucose (mg/DL) | | | |
|---|---|---|---|---|
| Group | 0 min | 30 min | 60 min | 90 min |
| Control group | 515.7 +/− 30.6 | 873 +/− 36.2 | 711.7 +/− 47.0 | 587.3 +/− 33.2 |
| Insulin group | 522.5 +/− 27.1 | 695.8 +/− 18.7** | 593.3 +/− 16.2* | 486.2 +/− 9.6* |
| Insulin + HC group | 501.7 +/− 19.3 | 575.2 +/− 30.5*** ## | 512.3 +/− 19.2** ## | 462.3 +/− 16.9** |

The data is expressed with mean +/− standard error (SEM). P values are calculated by t-test of Sigma Statistical Software, wherein $p < 0.05$ is considered significant and marked with the symbol "*";
$p < 0.01$ is considered highly significant and marked with the symbol "**" or "##"; and
$p \le 0.001$ is considered very highly significant and marked with the symbol "***". (* represents the comparison between the insulin group or the insulin + HC group and the control group; # represents the comparison between the insulin group and the insulin + HC group.)

As shown in the table, when compared with the control group, the blood glucose levels at interval of 30 minutes after administration of glucose were highly significantly reduced and that at intervals of 60 and 90 minutes after administration of glucose were significantly reduced, in the insulin group. When compared with the insulin group, the blood glucose levels at intervals of 30 and 60 minutes after administration of glucose were more significantly reduced in the insulin+HC group.

Example 8

Figure 8:
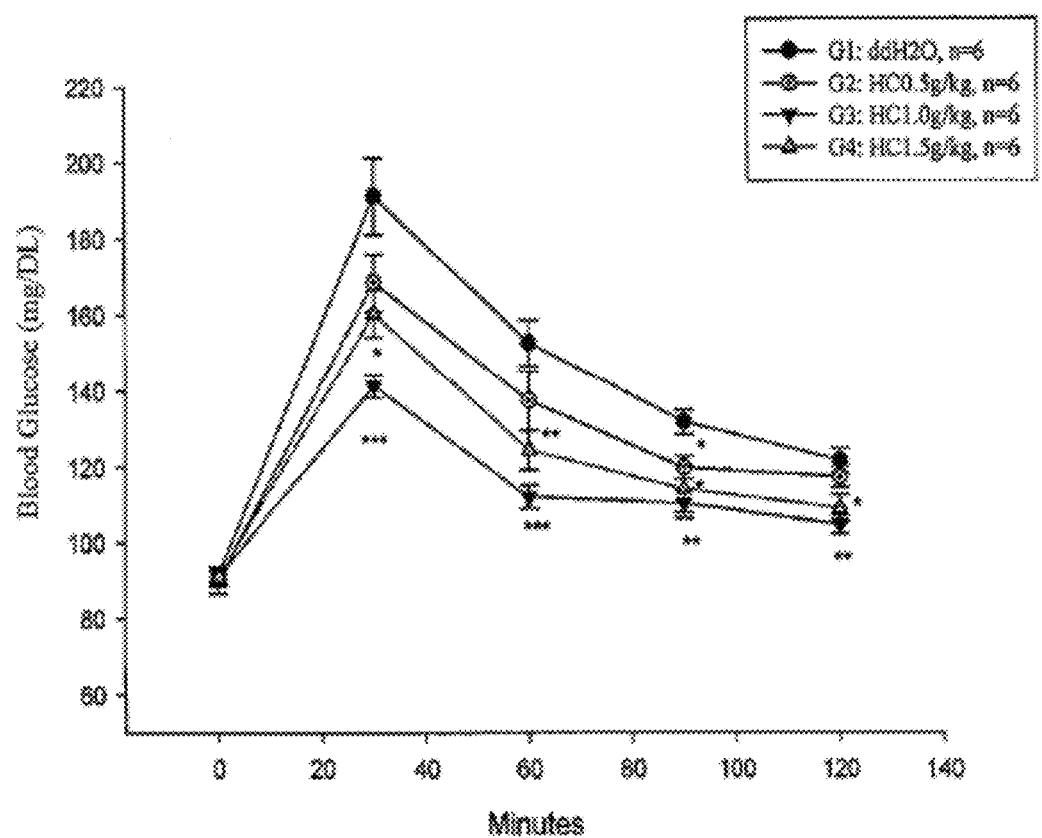
FIG. 8 illustrates the effect of water extract of the leaves and pseudostems of *Hedychium coronarium Koenig* in reducing blood glucose in normal rats in the glucose tolerance test. "G1: $ddH_2O$" represents oral administration of $H_2O$; "G2: HC 0.5 g/kg" represents oral administration of 0.5 g/kg water extract of leaves and pseudostems of *Hedychium coronarium Koenig*; "G3: HC 1.0 g/kg" represents oral administration of 1.0 g/kg water extract of leaves and pseudostems of *Hedychium coronarium Koenig*; and "G4: HC 1.5 g/kg" represents oral administration of 1.5 g/kg water extract of leaves and pseudostems of *Hedychium coronarium Koenig*. The X axis represents the time intervals of blood sampling, and the Y axis represents the concentration of blood glucose.

Glucose Tolerance Test of Water Extract of Leaves and Pseudostems of *Hedychium coronarium Koening* in Normal Rats The test rats and procedures were as described in Example 1. However, in this example, 24 Sprague-Dawley rats were divided into four groups: the placebo group (6 rats, to be administered with water), the 0.5 g/kg HC group (6 rats, to be administered with 0.5 g/kg water extract of leaves and pseudostems of *Hedychium coronarium Koening* ), the 1 g/kg HC group (6 rats, to be administered with 1 g/kg water extract of leaves and pseudostems of *Hedychium coronarium Koening* ) and the 1.5 g/kg HC group (6 rats, to be administered with 1.5 g/kg water extract of the leaves and pseudostems of *Hedychium coronarium Koening* ). After 30 minutes, each rat was administered with glucose at a total amount of 5 g/kg, orally (2.5 g/kg) and subcutaneously (2.5 g/kg). Blood was drawn from each animal at 30-minute intervals for the measurement of glucose (mg/DL). The results are shown in the table below and FIG. 8.

| | Concentration of blood glucose (mg/DL) | | | | |
|---|---|---|---|---|---|
| Group | 0 min | 30 min | 60 min | 90 min | 120 min |
| Placebo group (G1) | 91.7 +/− 2.2 | 190.8 +/− 9.9 | 152.5 +/− 6.0 | 131.7 +/− 3.2 | 121.5 +/− 3.1 |
| 0.5 g/kg HC group (G2) | 90.2 +/− 3.5 | 168.3 +/− 7.4 | 137.3 +/− 7.9 | 119.7 +/− 7.4* | 117.2 +/− 2.7 |
| 1 g/kg HC group (G3) | 91.0 +/− 2.0 | 141.2 +/− 3.0*** | 111.8 +/− 3.1*** | 110.2 +/− 3.9** | 104.5 +/− 2.4** |
| 1.5 g/kg HC group (G4) | 90.8 +/− 2.3 | 160.2 +/− 6.1* | 124.3 +/− 5.2** | 114 +/− 6.1* | 108.8 +/− 3.6* |

The data is expressed with mean +/− standard error (SEM). P values are calculated by t-test of Sigma Statistical Software, wherein $p < 0.05$ is considered significant and marked with the symbol "*";
$p < 0.01$ is considered highly significant and marked with the symbol "**"; and
$p \le 0.001$ is considered very highly significant and marked with the symbol "***".

The results show that when compared with the control group, 1 g/kg water extract of leaves and pseudostems of *Hedychium coronarium* has a highly significant effect in reducing blood glucose at 30 and 60 minutes after administration of glucose and has a very highly significant effect in reducing blood glucose at 90 and 120 minutes after administration of glucose.

Example 9

Figure 9:
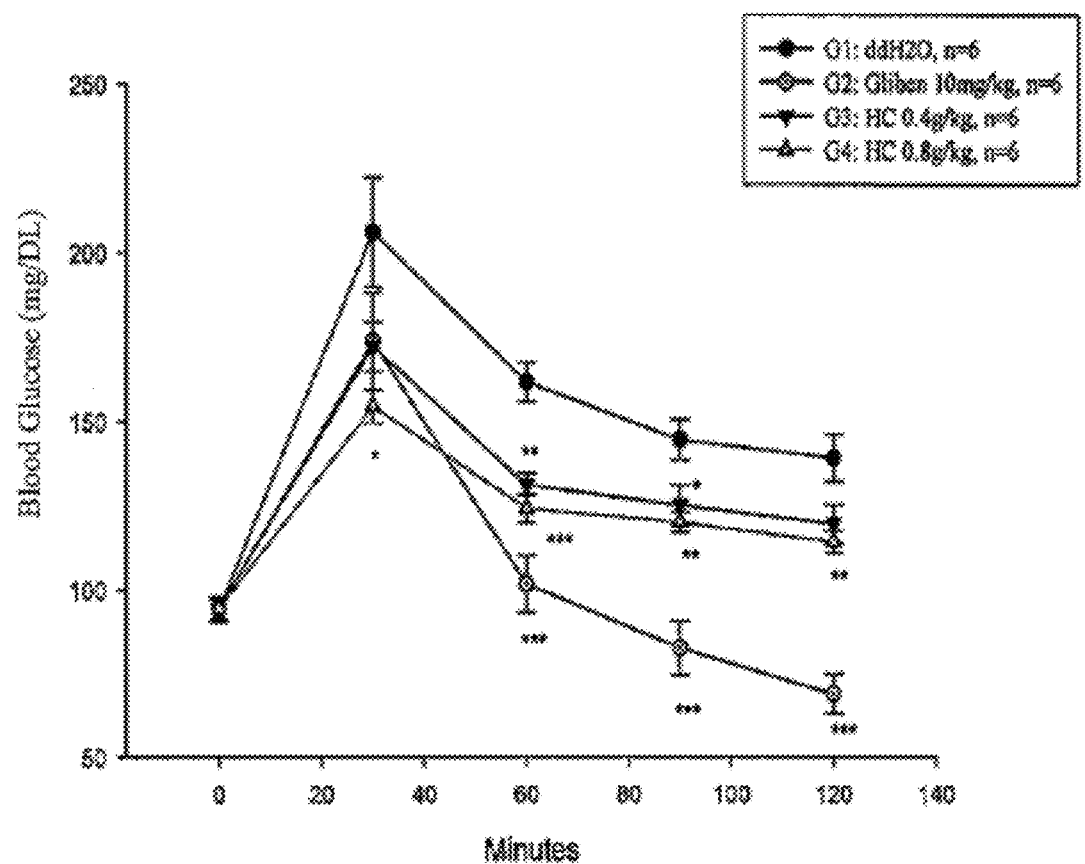
FIG. 9 illustrates the effect of water-ethanol extract of the leaves and pseudostems of *Hedychium coronarium Koenig* in reducing blood glucose in normal rats in the glucose tolerance test. "G1: $ddH_2O$" represents oral administration of $H_2O$; "G2: Gliben 10 mg/kg" represents oral administration of 10 mg/kg glibenclamide; "G3: HC 0.4 g/kg" represents oral administration of 0.4 g/kg water-ethanol extract of leaves and pseudostems of *Hedychium coronarium Koenig*; and "G4: HC 0.8 g/kg" represents oral administration of 0.8 g/kg water-ethanol extract of leaves and pseudostems of *Hedychium coronarium Koenig*. The X axis represents the time intervals of blood sampling, and the Y axis represents the concentration of blood glucose.

Glucose Tolerance Test of water-ethanol Extract of Leaves and Pseudostems of *Hedychium coronarium Koening* in Normal Rats The test rats and procedure were as those in Example 1. However, in this example, 24 Sprague-Dawley rats were divided into four groups: the placebo group (6 rats, to be administered with water), the positive control group (6 rats, to be administered with 10 mg/kg glibenclamide), the 0.4 g/kg HC group (6 rats, to be administered with 0.4 g/kg water-ethanol extract of leaves and pseudostems of *Hedychium coronarium Koening* ), and the 0.8 g/kg HC group (6 rats, to be administered with 0.8 g/kg water-ethanol extract of leaves and pseudostems of *Hedychium coronarium Koening* ). After 30 minutes, each rat was administered with glucose at a total amount of 5 g/kg, orally (2.5 g/kg) and subcutaneously (2.5 g/kg). Blood was drawn from each animal at 30-minute intervals for the measurement of glucose (mg/DL). The results are shown in the table below and FIG. 9.

| Group | Concentration of blood glucose (mg/DL) | | | | |
|---|---|---|---|---|---|
| | 0 min | 30 min | 60 min | 90 min | 120 min |
| Placebo group (G1) | 94.3 +/− 2.8 | 206 +/− 16.3 | 161.7 +/− 5.8 | 144.7 +/− 6.1 | 139.3 +/− 6.9 |
| Glibenclamide group (G2) | 94.3 +/− 3.8 | 173.8 +/− 14.5*** | 101.8 +/− 8.4*** | 82.7 +/− 8.1*** | 68.8 +/− 5.9*** |
| 0.4 g/kg HC group (G3) | 94.3 +/− 3.1 | 172.2 +/− 7.3 | 131.3 +/− 3.4** | 125.3 +/− 6.0* | 119.8 +/− 5.8 |
| 0.8 g/kg HC group (G4) | 94.5 +/− 3.1 | 154.5 +/− 4.9* | 124.3 +/− 4.2*** | 120.3 +/− 3.0* | 114.5 +/− 3.3** |

The data is expressed with mean +/− standard error (SEM). P values are calculated by t-test of Sigma Statistical Software, wherein $p < 0.05$ is considered significant and marked with the symbol "*";
$p < 0.01$ is considered highly significant and marked with the symbol "**";
and $p \leq 0.001$ is considered very highly significant and marked with the symbol "***".

The results show that when compared with the control group, 0.8 g/kg water-ethanol extract of leaves and pseudostems of *Hedychium coronarium Koening* has a significant effect in reducing blood glucose at 30 minutes after administration of glucose, a very highly significant effect in reducing blood glucose at 60 minutes after administration of glucose, and a highly significant effect in reducing blood glucose at 90 and 120 minutes after administration of glucose.

Example 10

Glucose Tolerance Test of Water Extract of Rhizomes of *Hedychium Coronarium Koening* in Normal Rats The test rats and procedures were as described in Example 1. However, in this example, 24 Sprague-Dawley rats were divided into four groups: the placebo group (6 rats, to be administered with water), the 0.5 g/kg HC group (6 rats, to be administered with 0.5 g/kg water extract of the rhizome of *Hedychium coronarium Koening*), the 1 g/kg HC group (6 rats, to be administered with 1 g/kg water extract of the rhizome of *Hedychium coronarium Koening* ), and the 1.5 g/kg HC group (6 rats, to be administered with 1.5 g/kg water extract of the rhizome of *Hedychium coronarium Koening* ). After 30 minutes, each rat was administered with glucose at a total amount of 5 g/kg, orally (2.5 g/kg) and subcutaneously (2.5 g/kg). Blood was drawn from each animal at 30-minute intervals for the measurement of glucose (mg/DL). The results are shown in the table below.

| Group | Concentration of blood glucose (mg/DL) | | | | |
|---|---|---|---|---|---|
| | 0 min | 30 min | 60 min | 90 min | 120 min |
| Placebo group | 92.3 +/− 5.7 | 242.3 +/− 13.1 | 160.7 +/− 5.4 | 146.2 +/− 6.7 | 125.8 +/− 3.8 |
| 0.5 g/kg HC group | 90.2 +/− 4.0 | 246.3 +/− 17.1 | 151.7 +/− 2.9 | 135.3 +/− 3.9 | 126 +/− 5.2 |

| Group | Concentration of blood glucose (mg/DL) | | | | |
|---|---|---|---|---|---|
| | 0 min | 30 min | 60 min | 90 min | 120 min |
| 1 g/kg HC group | 89.2 +/− 3.7 | 233.5 +/− 18.8 | 159.3 +/− 13.8 | 140 +/− 8.1 | 124.2 +/− 7.9 |
| 1.5 g/kg HC group | 89.5 +/− 3.3 | 218.8 +/− 10.9 | 152.7 +/− 5.9 | 146 +/− 5.0 | 129.7 +/− 3.9 |

The data is expressed with mean +/− standard error (SEM). P values are calculated by t-test of Sigma Statistical Software, wherein $p < 0.05$ is considered significant and marked with the symbol "*";
$p < 0.01$ is considered highly significant and marked with the symbol "**";
and $p \leq 0.001$ is considered very highly significant and marked with the symbol "***".

The results show that when compared with the control group, no significant differences were observed in the concentrations of blood glucose at all time points after administration of glucose in the rats administered with various doses of the water extracts of the rhizome of *Hedychium coronarium Koening*. It indicates that water extracts of the rhizome of *Hedychium coronarium Koening* do not have an effect in the reduction of blood glucose.

Example 11

Glucose Tolerance Test of Water-Ethanol Extract of Rhizomes of *Hedychium Coronarium Koening* in Normal Mice The test mice were fasted for 14 hours and then allowed to feed freely for one hour. Subsequently, 24 C57BL/6 mice were divided into four groups: the placebo group (6 mice, to be administered with 10% Tween 20), the 0.5 g/kg HC group (6 mice, to be administered with 0.5 g/kg water-ethanol extract of rhizomes of *Hedychium coronarium Koening*), the 1.0 g/kg HC group (6 mice, to be administered with 1.0 g/kg water-ethanol extract of rhizomes of *Hedychium coronarium Koening*), and the 1.5 g/kg HC group (6 mice, to be administered with 1.5 g/kg water-ethanol extract of rhizomes of *Hedychium coronarium Koening*). After 30 minutes, the mice were intra-abdominally administered with glucose (1.5 g/kg) for the glucose tolerance test. Blood was drawn from each animal at 30-minute intervals for the measurement of glucose (mg/DL). The results are shown in the table below.

| Group | Concentration of blood glucose (mg/DL) | | | |
|---|---|---|---|---|
| | 0 min | 30 min | 60 min | 90 min |
| Placebo group | 109.7 +/− 5.5 | 228.5 +/− 16.1 | 127.3 +/− 3.6 | 109.2 +/− 5.5 |
| 0.5 g/kg HC group | 111.5 +/− 4.0 | 223 +/− 9.3 | 138 +/− 5.5 | 111 +/− 5.9 |
| 1 g/kg HC group | 111.8 +/− 3.8 | 216 +/− 20.1 | 134.7 +/− 6.5 | 105.2 +/− 3.5 |
| 1.5 g/kg HC group | 109.5 +/− 4.4 | 215 +/− 14.4 | 135.5 +/− 9.7 | 114 +/− 4.4 |

The data is expressed with mean +/− standard error (SEM). P values are calculated by t-test of Sigma Statistical Software, wherein $p < 0.05$ is considered significant and marked with the symbol "*";
$p < 0.01$ is considered highly significant and marked with the symbol "**";
and $p \leq 0.001$ is considered very highly significant and marked with the symbol "***."

The results show that when compared with the control group, no significant differences were observed in the concentrations of blood glucose at all time points after administration of glucose in the mice administered with various doses of the water-ethanol extracts of rhizomes of *Hedychium coronarium Koening*. It indicates that water-ethanol extracts of rhizomes of *Hedychium coronarium Koening* do not have an effect in the reduction of blood glucose.

Example 12

Preparation of 95% Ethanol Extract of Leaves and Pseudostems of *Hedychium coronarium Koening*

Figure 10:
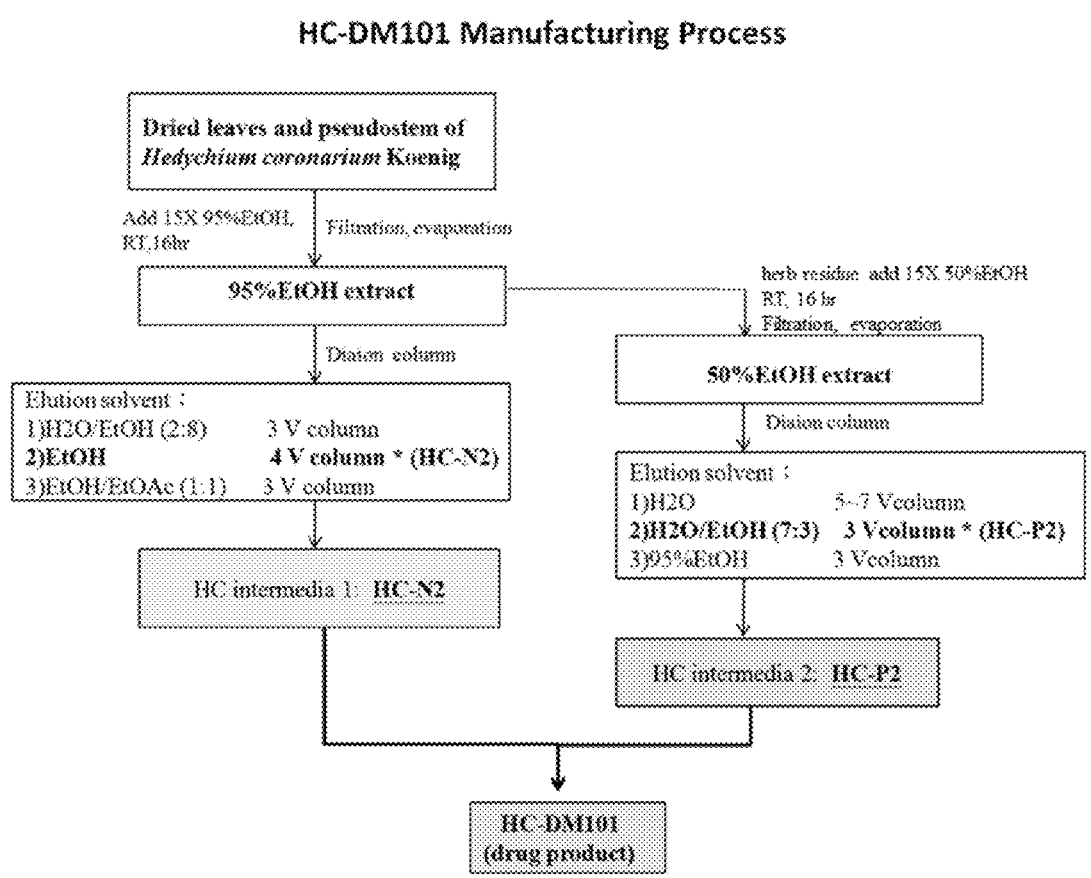
FIG. 10 shows the extraction procedure of leaves and pseudostems of *Hedychium coronarium Koenig* according to the present invention.

Dried powder of leaves and pseudostems of *Hedychium coronarium Koening* was soaked in 10-fold volume of 95% ethanol (w:v=1:10) and stirred for 16 hours. The resulted mixture was then filtered by vacuum filtration and the filtrate was collected. The powder (residue) obtained after the first filtration was soaked in 10-fold volume of 95% ethanol (w:v=1:10) and stirred for 16 hours, and the filtrate was collected. The filtrate collected from two runs of filtration was combined together and concentrated under reduced pressure to obtain a 95% ethanol extract of leaves and pseudostems of *Hedychium coronarium Koening*, which was then concentrated and dried and weighed. The procedure of the extraction is described in FIG. 10.

Example 13

Preparation of the Isolated Product (HC-N2) of the 95% Ethanol Extract of Leaves and Pseudostems of *Hedychium coronarium Koening*

The 95% ethanol extract of leaves and pseudostems of *Hedychium coronarium Koening* was isolated using a DIAION macroporous resin column HP20. Briefly, 20-fold weight of DIAION macroporous resin (compared with the 95% ethanol extract) was weighed and activated by ethanol. The activated resin was then loaded onto the column (10 cm×120 cm) by a wet method and eluted by ethanol until no white turbidity appears when the ethanol eluate was mixed with water at a ratio of 2:1. The resin was then repeatedly washed with water until no odor of ethanol was present and the level of the resin in the column remained the same. A given amount of *Hedychium coronarium Koening* samples (leaves and pseudostems) was soaked in 15-fold volume of 95% ethanol and stirred for 16 hours. Such extraction was conducted for two times. The resultant filtrate was collected and concentrated under reduced pressure to a volume of 5% of the original volume (about 0.5 fold of the original weight of the plant sample). The concentrate was then diluted with a mixture of 95% ethanol and water (8:2) and loaded onto the pretreated DIAION macroporous resin column. Preabsorption was performed for 1 hour. The flow rate was kept at around 0.5 BV/H. Elution was carried out by using a solution of water and 95% ethanol at a volume ratio of 2:8 (i.e. 1:4), 95% ethanol, and a solution of 95% ethanol and acetyl ester at a volume ratio of 1:1 in order. The elution rate was kept at around 2BV/H. Three to four fold column volume of the eluent was used for each concentration. The active ingredients for reducing blood glucose in the 95% ethanol extract of leaves and pseudostems of *Hedychium coronarium Koening* were found mostly in the eluate fraction from 95% ethanol. The eluate fraction was collected, concentrated, dried and weighed. The procedure of the extraction is described in FIG. 10.

Example 14

Preparation of 50% Ethanol Extract of Leaves and Pseudostems of *Hedychium coronarium Koening*

A given amount of *Hedychium coronarium Koening* samples (leaves and pseudostems) was extracted with 95% ethanol for two times as described in Example 13. The resulting residue was collected and weighed, and soaked in 15-fold volume of 50% ethanol and stirred for 16 hours. Such extraction was conducted for two times. The resultant filtrate was collected and concentrated under reduced pressure to a volume of 5% of the original volume (about 0.5 fold of the original weight of the plant sample). The procedure of the extraction is described in FIG. 10.

Example 15

Preparation of the Isolated Product (HC-P2) of the 50% Ethanol Extract of Leaves and Pseudostems of *Hedychium coronarium Koening*

20-fold weight of DIAION macroporous resin (compared with the 50% ethanol extract) was weighed and activated by ethanol. The activated resin was then loaded onto the column (10 cm×120 cm) by a wet method and eluted by ethanol until no white turbidity appears when the ethanol eluate was mixed with water at a ratio of 2:1. The resin was then repeatedly washed with water until no odor of ethanol was present and the level of the resin in the column remained the same. The residues collected from two runs of filtration of *Hedychium coronarium Koening* samples (leaves and pseudostems) with 95% ethanol was soaked in 15-fold volume of 95% ethanol and stirred for 16 hours. Such extraction was conducted for two times. The resultant filtrate was collected and concentrated under reduced pressure to a volume of 5% of the original volume (about 0.5 fold of the original weight of the plant sample). The concentrate was then diluted with an aqueous solution and loaded onto the pretreated DIAION macroporous resin column. Preabsorption was performed for 1 hour. The flow rate was kept at around 0.5 BV/H. Elution was carried out by using water, 30% ethanol and 95% ethanol in order. The elution rate was kept at around 2 BV/H. Three to five fold column volume of the eluent was used for each concentration. The active ingredients for reducing blood glucose in the 50% ethanol extract of leaves and pseudostems of *Hedychium coronarium Koening* were found mostly in the eluate fraction from 30% ethanol. The eluate fraction was collected, concentrated, dried and weighed. The procedure of the extraction is described in FIG. 10.

Example 16

Composition of the Isolated Product (HC-N2) of the 95% Ethanol Extract of Leaves and Pseudostems of *Hedychium coronarium Koening* and the Isolated Product (HC-P2) of the 50% Ethanol Extract of Leaves and Pseudostems of *Hedychium coronarium Koening*

The isolated product (HC-N2) of the 95% ethanol extract of leaves and pseudostems of *Hedychium coronarium Koening* obtained in Example 13 and the isolated product (HC-P2) of the 50% ethanol extract of leaves and pseudostems of *Hedychium coronarium Koening* obtained in Example 15 were combined to produce a composition, named DM101. The procedure of the extraction is described in FIG. 10.

Example 17

Preparation of Water Extract of Leaves and Pseudostems of *Hedychium coronarium Koening*

Dried powder of leaves and pseudostems of *Hedychium coronarium Koening* was added to 10-fold volume of hot water (w:v=1:10) and stirred with heat for 1 hour. The resultant mixture was then filtered by vacuum filtration, and the filtrate was collected. The residue as obtained was added to 10-fold volume of hot water (w:v=1:10) and stirred with heat for 1 hour, and the filtrate was collected. The filtrate collected from two runs of filtration was combined together and concentrated under reduced pressure to obtain a water extract of leaves and pseudostems of *Hedychium coronarium Koening*, which was then concentrated and dried and weighed.

Example 18

Analysis of Components in Ethanol Extract of Leaves and Pseudostems of *Hedychium coronarium Koening*

The ethanol extract of leaves and pseudostems of *Hedychium coronarium Koening* was analyzed by high performance liquid chromatography (HPLC). The instruments and apparatuses are as follows:
Pump: Spectra-Physics P1000;
Autosampler: SpectraSYSTEM AS3000;
Detector: Surveyor PDA Plus;
Sample injection: 10 μL;
Column: Thermo, BDS HYPERSIL C18, 4.6 (inner diameter)*250 mm (length), 5 μm (particle size);
Elution procedure: methanol-water (MeOH-$H_2O$) gradient elution or acetonitrile-water (0.1% trifluoroacetic acid) gradient elution;
Column oven: 35° C.;

Flow rate: 1.0 mL/min;
PDA condition: sampling: 0.64 sec;
Wave length range: 190-370 nm, channel: 254 nm.

Figure 11:
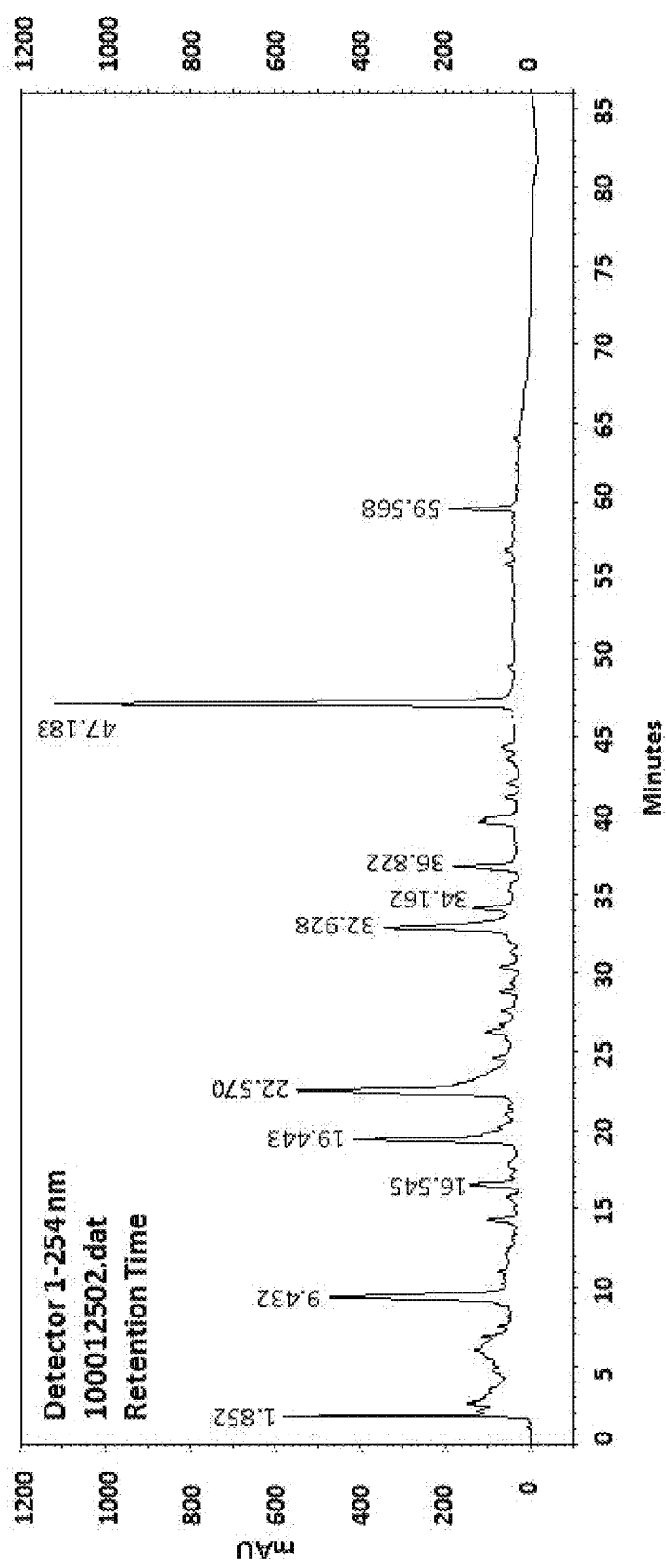
FIG. 11 shows the chemical fingerprint analyses of (A) the isolated product of 95% ethanol extract HC-N2, (B) the isolated product of 50% ethanol extract HC-P2, and (C) the tablet of the combined product (DM101) of HC-N2 and HC- P2 where upper part is obtained in a condition using a linear gradient of methanol and water and the lower part is obtained in a condition using a linear gradient of acetonitrile (ACN) and water containing 0.1% trifluoroacetic acid (TFA).
Figure 11:
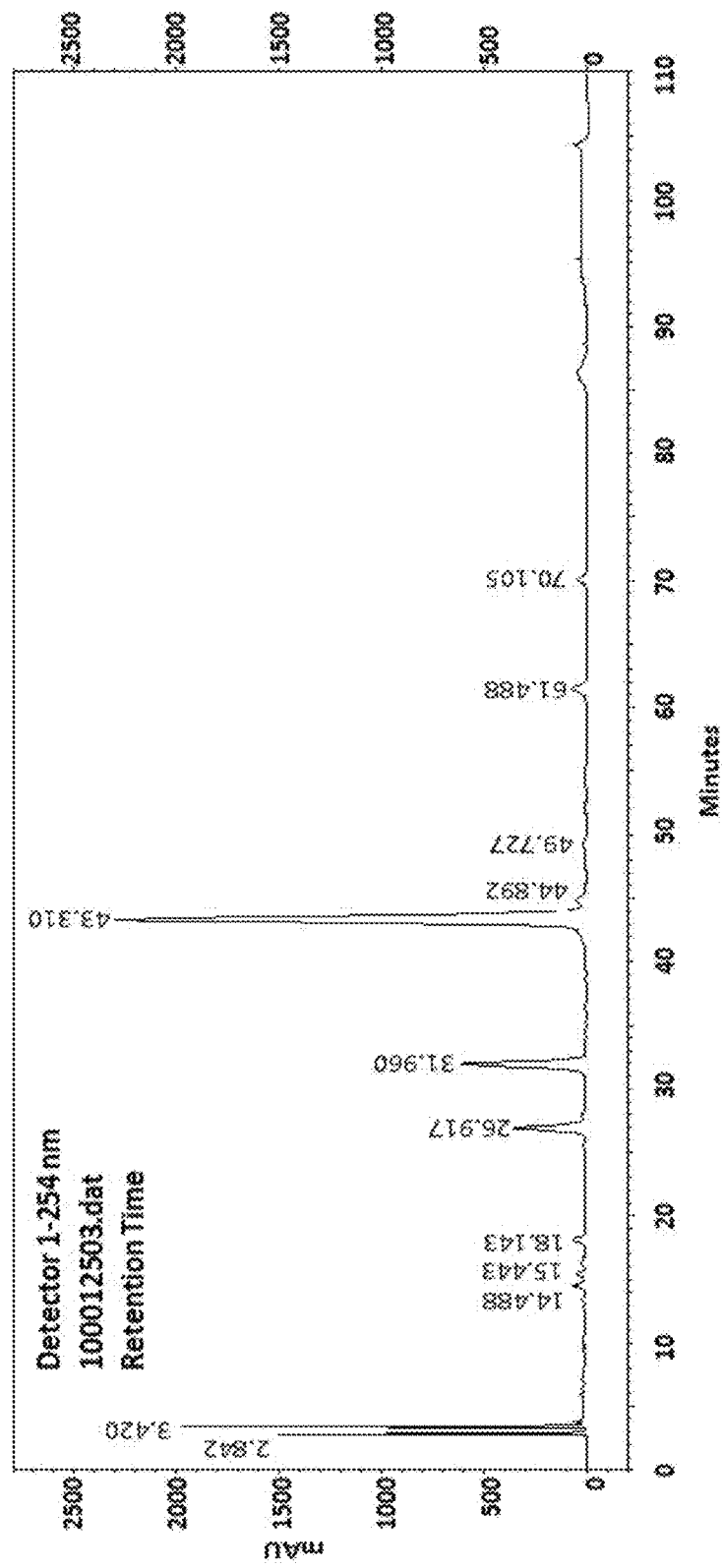
Figure 11:
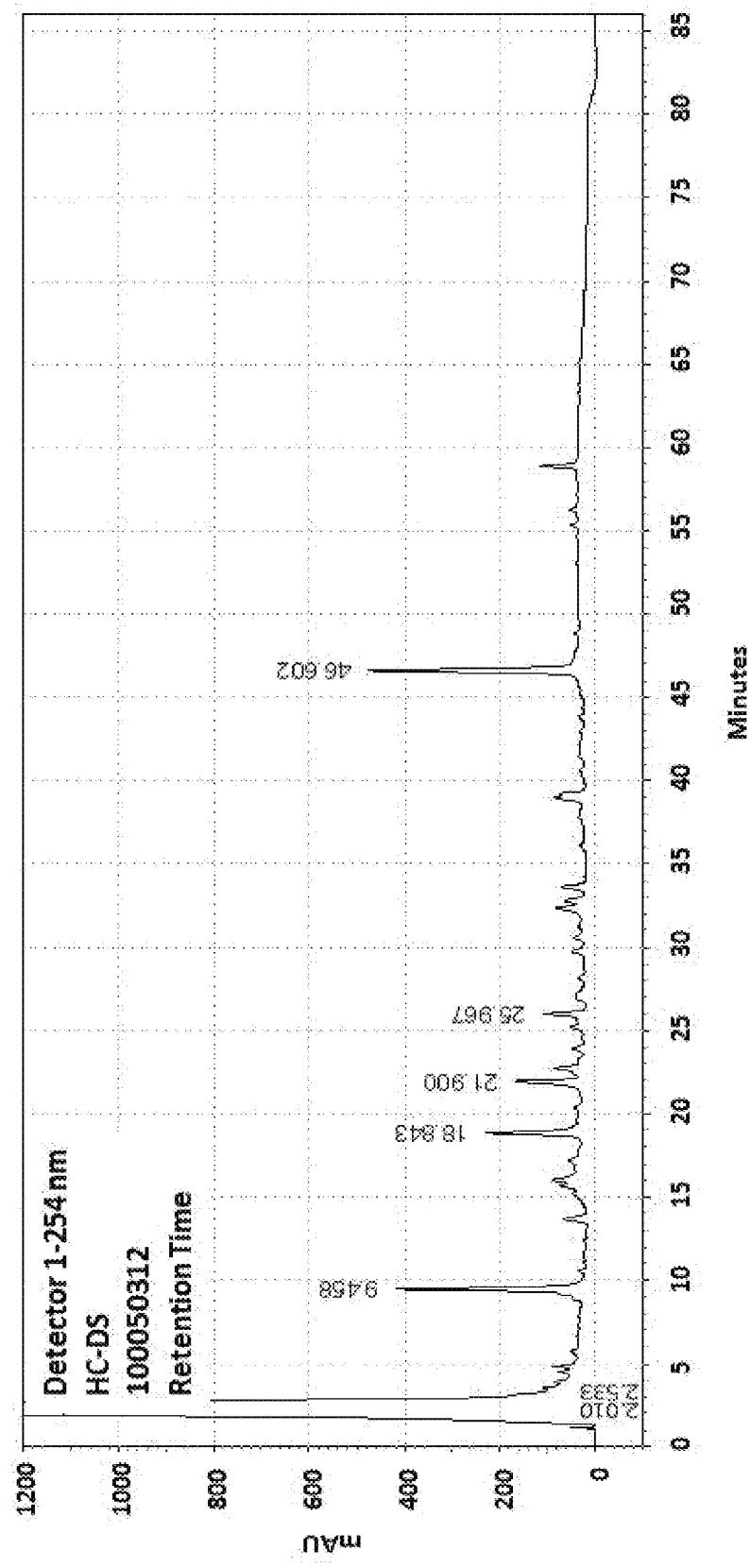
Figure 11:
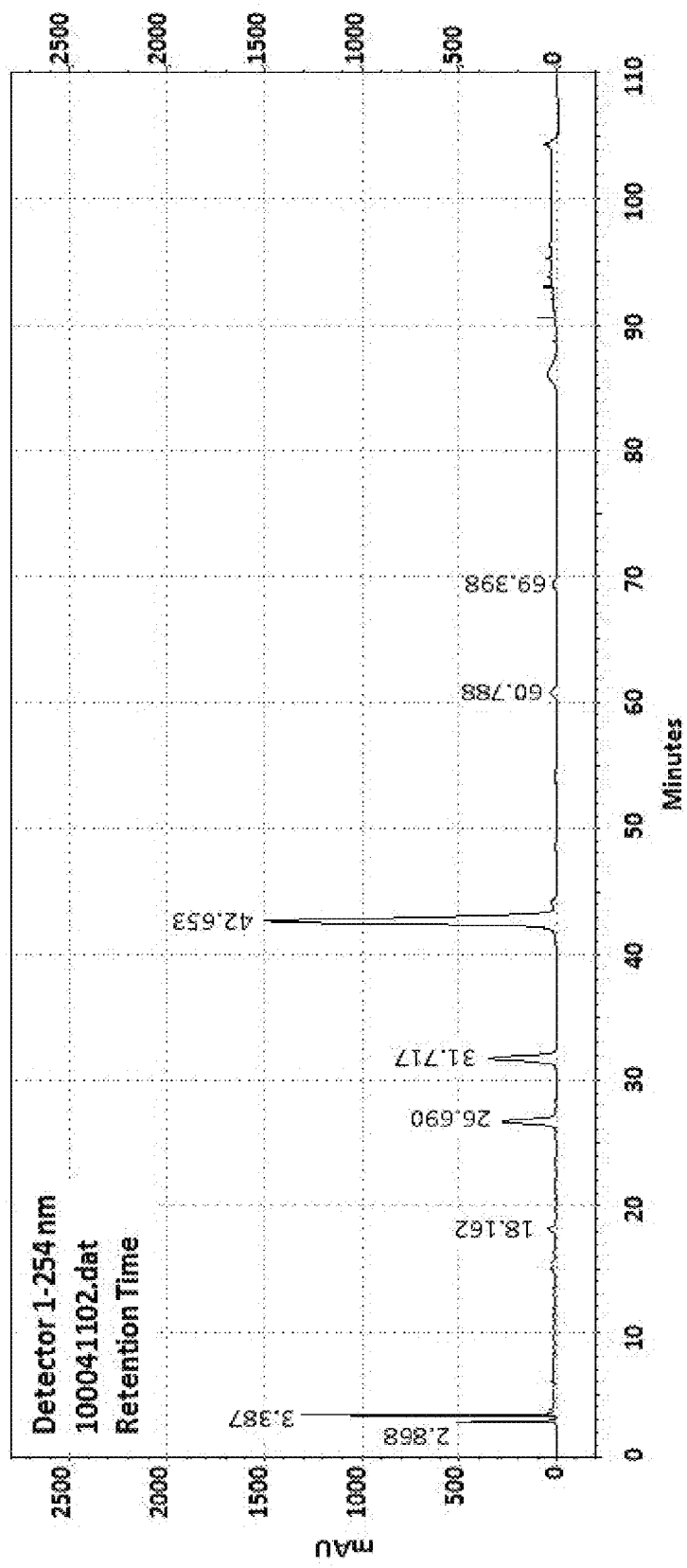

FIG. 11 (A) shows the chemical fingerprint analysis of the isolated product (HC-N2) of the 95% ethanol extract of leaves and pseudostems of *Hedychium coronarium Koening*. The result demonstrates that the isolated product HC-N2 of the 95% ethanol extract of leaves and pseudostems of *Hedychium coronarium Koening* had HPLC peaks with the following retention times:

| No. of peaks | Retention time (min) |
| --- | --- |
| 1 | 9.4 |
| 2 | 19.4 |
| 3 | 22.6 |
| 4 | 32.9 |
| 5 | 36.8 |
| 6 | 47.2 |
| 7 | 59.5 |

Four peaks at the retention time of 9.4, 19.4, 22.6 and 47.2 minutes are major and others at the retention time of 32.9, 36.8 and 59.5 are minor.

Mode 1 of elution is as follows:

| Mobile phase | Time (min) | | | | |
| --- | --- | --- | --- | --- | --- |
| | 0 | 60 | 76 | 78 | 86 |
| MeOH | 66% | 100% | 100% | 66% | 66% |
| H$_2$O | 34% | 0% | 0% | 34% | 34% |

FIG. 11 (B) shows the chemical fingerprint analysis of the isolated product (HC-P2) of the 50% ethanol extract of leaves and pseudostems of *Hedychium coronarium Koening*. The result demonstrates that the isolated product HC-P2 of the 50% ethanol extract of leaves and pseudostems of *Hedychium coronarium Koening* had HPLC peaks with the following retention times:

| No. of peaks | Retention time (min) |
| --- | --- |
| 1 | 26.9 |
| 2 | 31.9 |
| 3 | 43.3 |
| 4 | 61.4 |
| 5 | 70.1 |

Mode 2 of elution is as follows:

| Mobile phase | Time (min) | | | | | |
| --- | --- | --- | --- | --- | --- | --- |
| | 0 | 80 | 90 | 100 | 102 | 110 |
| ACN (+0.05%TFA) | 10% | 17% | 100% | 100% | 10% | 10% |
| H$_2$O (+0.05%TFA) | 90% | 83% | 0% | 0% | 90% | 90% |

The composition of the isolated products of the ethanol extract of leaves and pseudostems of *Hedychium coronarium Koening* (DM101) were mixed with microcrystalline cellulose to form tablets, which were then subject to chemical fingerprint analysis. The result was shown in FIG. 11 (C).

Example 19

Figure 12:
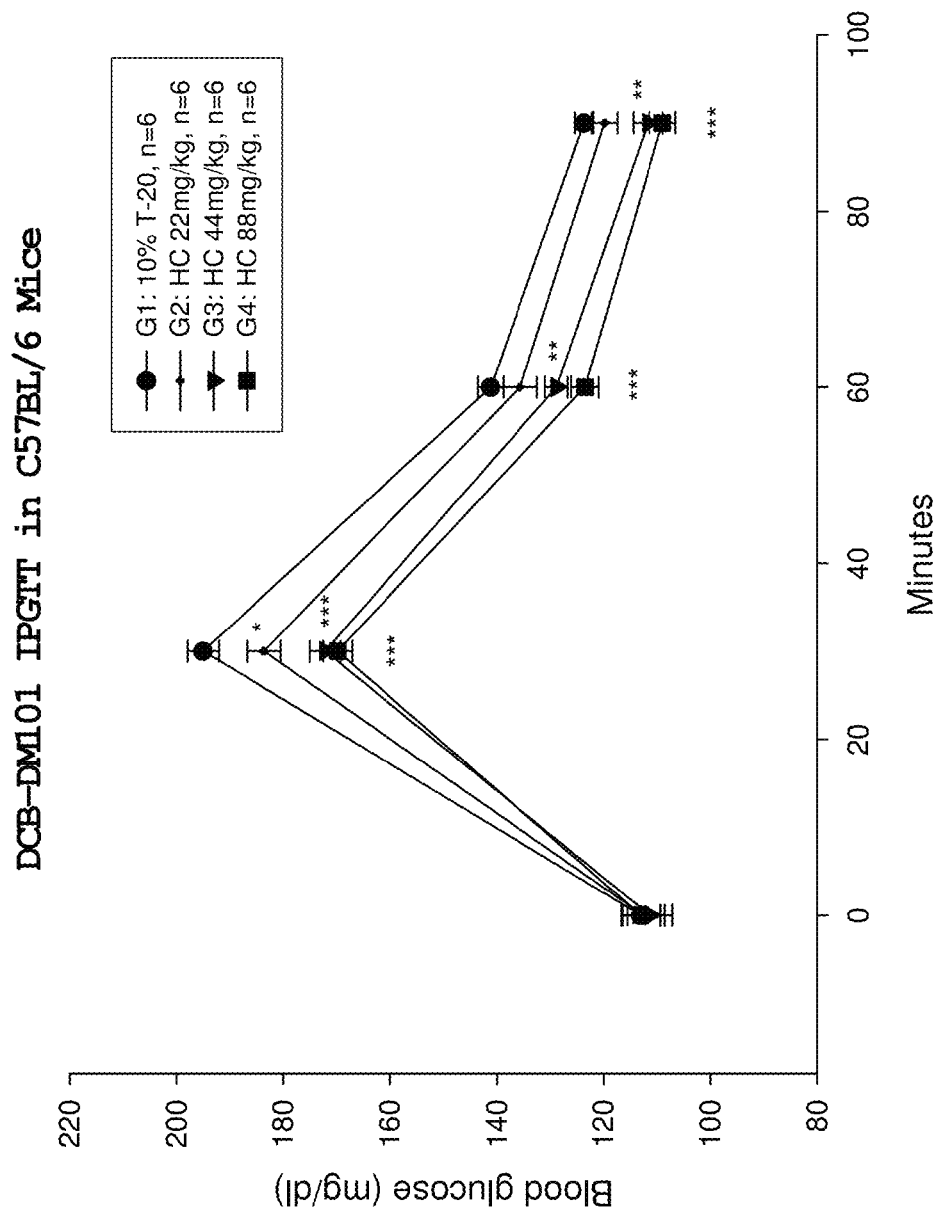
FIG. 12 illustrates the effect of the combined product (DM101) of the isolated products of the ethanol extract of leaves and pseudostems of *Hedychium coronarium Koening* in normal mice. "G1" indicates oral administration of 10% Tween 20; "G2" indicates oral administration of 22 mg/kg DM101; "G3" indicates oral administration of 44 mg/kg DM101; and "G4" indicates oral administration of 88 mg/kg DM101. The X axis represents the time intervals of blood sampling, and the Y axis represents the concentration of blood glucose. P values are calculated by t-test of Sigma Statistical Software wherein $p<0.05$ is considered significant and marked with *; $p<0.01$ is considered highly significant and marked with ; and $p\leq0.001$ is considered very highly significant and marked with *.

Intraperitoneal Glucose Tolerance Test of the Composition DM101 of the Isolated Products of the Ethanol Extract of Leaves and Pseudostems of *Hedychium coronarium Koening* in Normal Mice Twenty-four (24) mice (C57BL/6 mice) were divided into four groups: the placebo group (6 mice, to be administered with 10% Tween 20), the 22 mg/kg DM101 group (6 mice, to be administered with 22 mg/kg DM101), the 44 mg/kg DM101 group (6 mice, to be administered with 44 mg/kg DM101), and the 88 mg/kg DM101 group (6 mice, to be administered with 88 mg/kg DM101). The mice were fasted for 14 hours and then allowed to feed freely for 1 hour. Subsequently, the placebo group was orally administered with 10% Tween 20; the 22 mg/kg DM101 group was orally administered with 22 mg/kg DM101; the 44 mg/kg DM101 group was orally administered with 44 mg/kg DM101; and the 88 mg/kg DM101 group was orally administered with 88 mg/kg DM101. After 30 minutes, each mouse was intraperitoneally administered with 1.5 g/kg glucose. Blood was drawn from each mouse at the intervals of 0, 30, 60, and 90 minutes for the measurement of glucose (mg/DL). The results are shown in the table below and FIG. 12.

| Group | Concentration of blood glucose (mg/DL) | | | |
| --- | --- | --- | --- | --- |
| | 0 min | 30 min | 60 min | 90 min |
| Placebo group (G1) | 114.8 +/− 3.3 | 198 +/− 4.3 | 151 +/− 3.5 | 129.8 +/− 2.2 |
| 22 mg/kg DM101 group (G2) | 115.2 +/− 2.7 | 180.5 +/− 2.6** | 136.7 +/− 2.6** | 117.7 +/− 2.6** |
| 44 mg/kg DM101 group (G3) | 114.8 +/− 2.5 | 168.8 +/− 2.7*** | 130.5 +/− 2.4*** | 117.8 +/− 2.0** |
| 88 mg/kg DM101 (G4) | 114.8 +/− 3.3 | 161.8 +/− 2.8*** | 125.7 +/− 1.5*** | 110 +/− 2.4*** |

The data is expressed with mean +/− standard error (SEM). P values are calculated by t-test of Sigma Statistical Software, wherein $p < 0.05$ is considered significant and marked with the symbol "*";
$p < 0.01$ is considered highly significant and marked with the symbol "**";
and $p \leq 0.001$ is considered very highly significant and marked with the symbol "***".

Moreover, the resultant percentages of decreased blood glucose are shown below:

| | Total AUC | AUC from 0 min |
| --- | --- | --- |
| G2 | 7.25% | 30.82% |
| G3 | 11.09% | 44.11% |
| G4 | 14.46% | 56.48% |

G2: the 22 mg/kg DM101 group, which was orally administered with 22 mg/kg DM101;
G3: the 44 mg/kg DM101 group, which was orally administered with 44 mg/kg DM101;
G4: the 88 mg/kg DM101 group, which was orally administered with 88 mg/kg DM101.

The results show that when compared with the placebo group, the blood glucose levels at intervals of 30, 60 and 90 minutes after administration of glucose were highly or very highly significantly reduced in the 22 mg/kg DM101 group, the 44 mg/kg DM101 group, and the 88 mg/kg DM101 group. It demonstrates that the blood glucose levels in normal mice can be significantly reduced by administration of DM101 at a concentration as low as 22 mg/kg. The efficacies of lowering blood glucose were 31%, 44% and 56%, respectively. Furthermore, administration of 44 mg/kg DM101, is sufficient to lower blood glucose in normal mice for more than 40%.

Example 20

Figure 13:
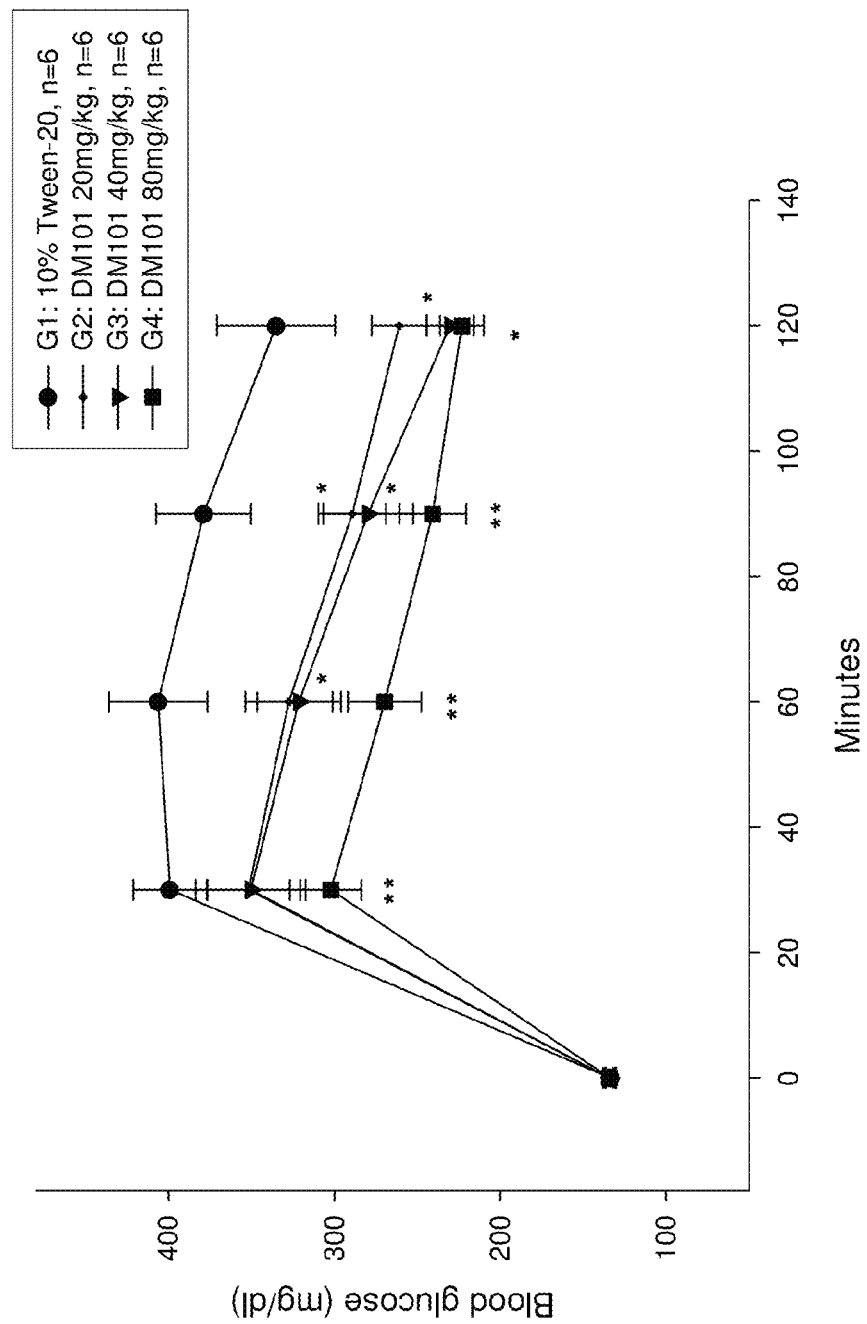
FIG. 13 illustrates the effect of the combined product (DM101) of the isolated products of the ethanol extract of leaves and pseudostems of *Hedychium coronarium Koening* in diabetic mice induced by high-fat diet. "G1" indicates oral administration of 10% Tween 20; "G2" indicates oral administration of 20 mg/kg DM101; "G3" indicates oral administration of 40 mg/kg DM101; and "G4" indicates oral administration of 80 mg/kg DM101. The X axis represents the time intervals of blood sampling, and the Y axis represents the concentration of blood glucose. P values are calculated by t-test of Sigma Statistical Software wherein $p<0.05$ is considered significant and marked with *; $p<0.01$ is considered highly significant and marked with ; and $p\leq0.001$ is considered very highly significant and marked with *.

Oral Glucose Tolerance Test of the Composition DM101 of the Isolated Products of the Ethanol Extract of Leaves and Pseudostems of *Hedychium coronarium Koening* in Mice Fed by High-Fat Diet Twenty-four (24) diabetic mice induced by high-fat diet (C57BL/6 mice) were divided into four groups: the placebo group (6 mice, to be administered with 10% Tween 20), the 20 mg/kg DM101 group (6 mice, to be administered with 20 mg/kg DM101), the 40 mg/kg DM101 group (6 mice, to be administered with 40 mg/kg DM101), and the 80 mg/kg DM101 group (6 mice, to be administered with 80 mg/kg DM101). The mice were fasted for 14 hours and then allowed to feed freely for 1 hour. After 4 hours, the placebo group was orally administered with 10% Tween 20; the 20 mg/kg DM101 group was orally administered with 20 mg/kg DM101; the 40 mg/kg DM101 group was orally administered with 40 mg/kg DM101; and the 80 mg/kg DM101 group was orally administered with 80 mg/kg DM101. After 30 minutes of the administration, each mouse was orally administered with 1.5 g/kg glucose. Blood was drawn from each mouse at the intervals of 0, 30, 60, 90, and 120 minutes for the measurement of glucose (mg/DL). The results are shown in the table below and FIG. 13.

minutes after administration of glucose were significantly reduced in the 40 mg/kg DM101 group; and the blood glucose levels at intervals of 30 and 60 minutes after administration of glucose were highly significantly reduced and that at interval of 120 minutes after administration of glucose were significantly reduced, in the 80 mg/kg DM101 group. It demonstrates that the blood glucose levels in diabetic mice induced by high-fat diet can be significantly reduced by administration of DM101 at a concentration as low as 40 mg/kg. The efficacies of lowering blood glucose were 31%, 33% and 49%, respectively. Furthermore, administration of 80 mg/kg DM101 of the isolated product of the ethanol extract of leaves and pseudostems of *Hedychium coronarium Koening* is sufficient to lower blood glucose in diabetic mice for more than 40%.

Example 21

Glucose Tolerance Test of Water Extract of Leaves and Pseudostems of *Hedychium coronarium Koening* in Normal Mice Twelve (12) mice (C57BL/6 mice) were divided into two groups: the placebo group (6 mice, to be administered with $H_2O$) and the 0.8 g/kg HC group (6 mice, to be administered with 0.8 g/kg water extract of the leaves and pseudostems of *Hedychium coronarium Koening* ). The mice were fasted for 14 hours and then allowed to feed freely for 1 hour. Subsequently, the placebo group was orally administered with $H_2O$, and the 0.8 g/kg HC group was orally administered with 0.8 g/kg water extract of leaves and pseudostems of *Hedychium coronarium Koening*. After 30 minutes, each mouse was intraperitoneally administered with 1.5 g/kg glucose. Blood was drawn from each mouse at the intervals of 0, 10, 30, 60,

|  | Concentration of blood glucose (mg/DL) | | | | |
| --- | --- | --- | --- | --- | --- |
| Group | 0 min | 30 min | 60 min | 90 min | 120 min |
| Placebo group (G1) | 133.5 +/− 2.9 | 399.2 +/− 22.2 | 406.2 +/− 29.7 | 378.8 +/− 28.6 | 335.2 +/− 35.6 |
| 20 mg/kg DM101 group (G2) | 134.3 +/− 2.5 | 351.7 +/− 24.8 | 327.3 +/− 26.4 | 289.2 +/− 20.3* | 260.8 +/− 16.6 |
| 40 mg/kg DM101 group (G3) | 134.3 +/− 3.4 | 350.5 +/− 33.2 | 321.3 +/− 25.2* | 279.7 +/− 27.1* | 230.2 +/− 14.2* |
| 80 mg/kg DM101 group (G4) | 134.0 +/− 3.8 | 302.2 +/− 18.5** | 269.7 +/− 22.2** | 240.7 +/− 20.1** | 223 +/− 13.2* |

The data is expressed with mean +/− standard error (SEM). P values are calculated by t-test of Sigma Statistical Software, wherein $p < 0.05$ is considered significant and marked with the symbol "*";
$p < 0.01$ is considered highly significant and marked with the symbol "**";
and $p \leq 0.001$ is considered very highly significant and marked with the symbol "***".

Figure 14:
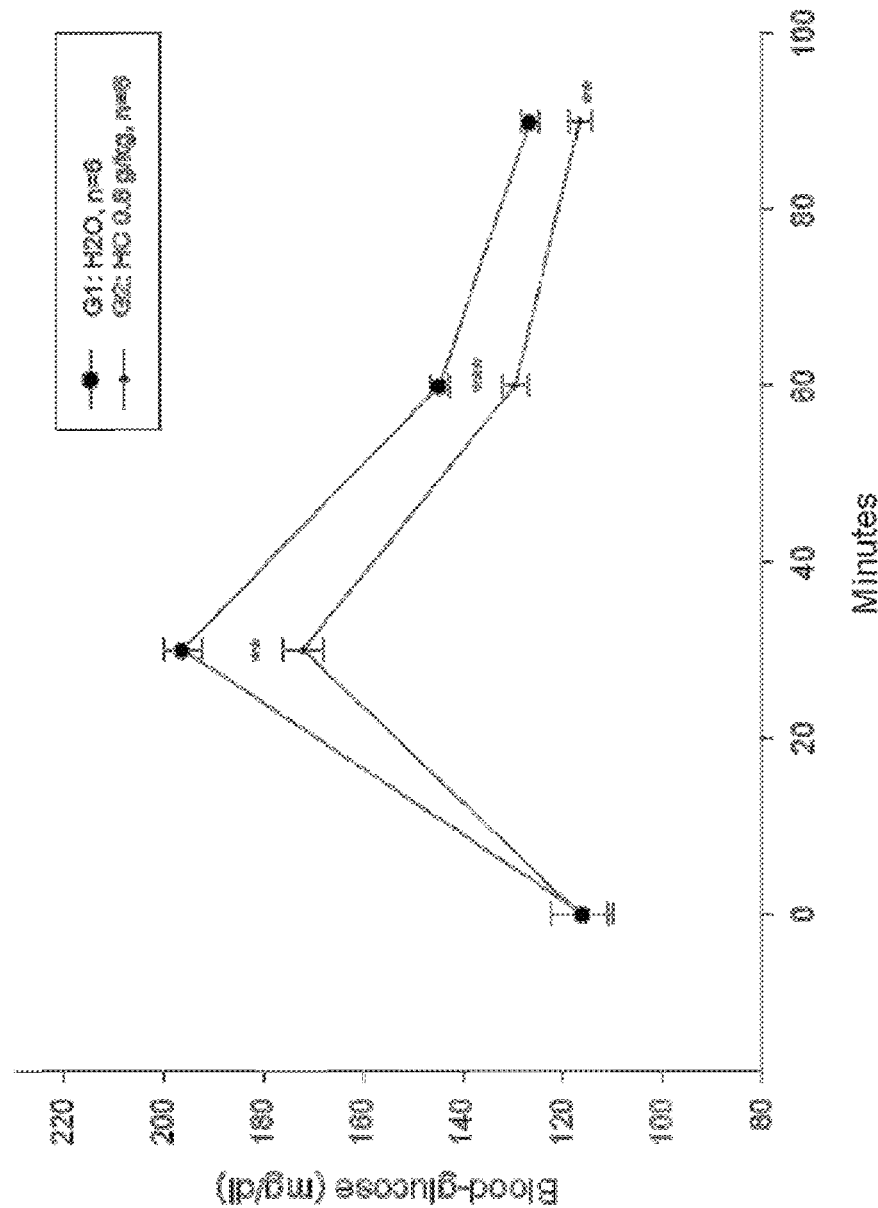
FIG. 14 illustrates the effect of the water extract of leaves and pseudostems of *Hedychium coronarium* in normal mice. "G1" indicates oral administration of water; and "G2" indicates oral administration of 0.8 g/kg water extract of the leaves and pseudostems of *Hedychium coronarium Koening*. The X axis represents the time intervals of blood sampling, and the Y axis represents the concentration of blood glucose. P values are calculated by t-test of Sigma Statistical Software wherein $p<0.05$ is considered significant and marked with *; $p<0.01$ is considered highly significant and marked with ; and $p\leq0.001$ is considered very highly significant and marked with *.

The results show that when compared with the placebo group, the blood glucose levels at intervals of 60, 90 and 120 and 90 minutes for the measurement of glucose (mg/DL). The results are shown in the table below and FIG. 14.

|  | Concentration of blood glucose (mg/DL) | | | |
| --- | --- | --- | --- | --- |
| Group | 0 min | 10 min | 30 min | 90 min |
| Placebo group | 115.8 +/− 6.2 | 196.2 +/− 3.9 | 144.7 +/− 1.9 | 126.5 +/− 1.7 |
| 0.8 g/kg HC group | 116.5 +/− 5.6 | 172 +/− 4.1** | 129.5 +/− 2.5*** | 116.5 +/− 2.3** |

The data is expressed with mean +/− standard error (SEM). P values are calculated by t-test of Sigma Statistical Software, wherein $p < 0.05$ is considered significant and marked with the symbol "*";
$p < 0.01$ is considered highly significant and marked with the symbol "**";
and $p \leq 0.001$ is considered very highly significant and marked with the symbol "***".

Moreover, the resultant percentages of decreased blood glucose are shown below:

|    | Total AUC | AUC from 0 min |
|----|-----------|----------------|
| G2 | 8.41%     | 40.17%         |

G2: the 0.8 g/kg HC group, which was orally administered with 0.8 g/kg water extract of the leaves and pseudostems of *Hedychium coronarium* Koening.

The results show that when compared with the placebo group, the blood glucose levels at intervals of 30, 60 and 90 minutes after administration of glucose were significantly reduced in the 0.8 g/kg HC group. The efficacy of lowering blood glucose was 40%. It also demonstrates that administration of 0.8 g/kg water extract of leaves and pseudostems of *Hedychium coronarium* Koening is needed to lower blood glucose levels in normal mice for more than 40%.

Example 22

Figure 15:
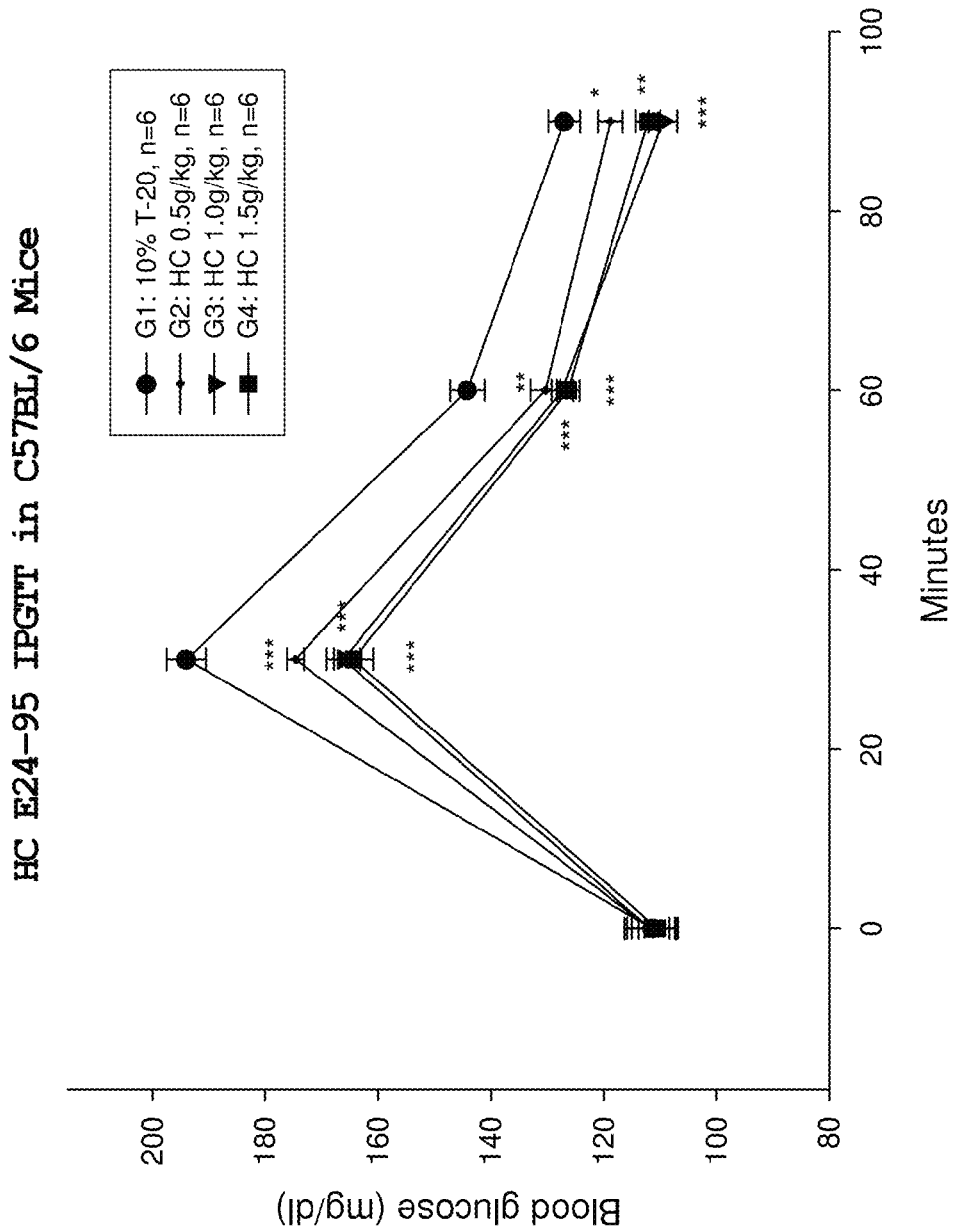
FIG. 15 illustrates the effect of 95% ethanol extract of leaves and pseudostems of *Hedychium coronarium Koening* in normal mice. "G1" indicates oral administration of 10% Tween 20; "G2" indicates oral administration of 0.5 g/kg 95% ethanol extract of leaves and pseudostems of *Hedychium coronarium*; "G3" indicates oral administration of 1.0 g/kg 95% ethanol extract of leaves and pseudostems of *Hedychium coronarium Koening*; and "G4" indicates oral administration of 1.5 g/kg 95% ethanol extract of leaves and pseudostems of *Hedychium coronarium Koening*. P values are calculated by t-test of Sigma Statistical Software wherein $p<0.05$ is considered significant and marked with *; $p<0.01$ is considered highly significant and marked with ; and $p\leq0.001$ is considered very highly significant and marked with *.

Glucose Tolerance Test of 95% Ethanol Extract of Leaves and Pseudostems of *Hedychium coronarium* Koening in Normal Mice Twenty-four (24) mice (C57BL/6 mice) were divided into four groups: the placebo group (6 mice, to be administered with 10% Tween 20), the 0.5 g/kg HC group (6 mice, to be administered with 0.5 g/kg 95% ethanol extract of leaves and pseudostems of *Hedychium coronarium* Koening ), the 1.0 g/kg HC group (6 mice, to be administered with 1.0 g/kg 95% ethanol extract of leaves and pseudostems of *Hedychium coronarium* Koening ), and the 1.5 g/kg HC group (6 mice, to be administered with 1.5 g/kg 95% ethanol extract of leaves and pseudostems of *Hedychium coronarium* Koening). The mice were fasted for 14 hours and then allowed to feed freely for 1 hour. Subsequently, the mice were orally administered with 10% Tween 20 (the placebo group), 0.5 g/kg of 95% ethanol extract of leaves and pseudostems of *Hedychium coronarium* Koening (the 0.5 g/kg HC group), 1.0 g/kg 95% ethanol extract of leaves and pseudostems of *Hedychium coronarium* Koening (the 1.0 g/kg HC group), and 1.5 g/kg 95% ethanol extract of leaves and pseudostems of *Hedychium coronarium* Koening (the 1.5 g/kg HC group). After 30 minutes, each mouse was intraperitoneally administered with 1.5 g/kg glucose. Blood was drawn from each mouse at the intervals of 0, 10, 30, 60, and 90 minutes for the measurement of glucose (mg/DL). The results are shown in the table below and FIG. 15.

|                       | Concentration of blood glucose (mg/DL) | | | |
|-----------------------|---------|---------------|----------------|----------------|
| Group                 | 0 min   | 10 min        | 30 min         | 60 min         |
| Placebo group (G1)    | 111.3 ± 4.5 | 194 ± 3.4     | 144.2 ± 3.0    | 127 ± 2.8      |
| 0.5 g/kg HC group (G2) | 111.7 ± 3.3 | 174.7 ± 1.5*** | 130.3 ± 2.6** | 118.8 ± 2.1*   |
| 1 g/kg HC group (G3)  | 111.8 ± 4.5 | 166.2 ± 2.9*** | 127.3 ± 1.9*** | 109.5 ± 2.5*** |
| 1.5 g/kg HC group (G4) | 110.5 ± 3.3 | 164.3 ± 3.5*** | 126.3 ± 2.0*** | 112.2 ± 2.2**  |

The data is expressed with mean +/− standard error (SEM). P values are calculated by t-test of Sigma Statistical Software, wherein p < 0.05 is considered significant and marked with the symbol "*";
p < 0.01 is considered highly significant and marked with the symbol "**";
and p ≤ 0.001 is considered very highly significant and marked with the symbol "***".

Moreover, the resultant percentages of decreased blood glucose are shown below:

|    | Total AUC | AUC from 0 min |
|----|-----------|----------------|
| G2 | 7.56%     | 30.88%         |
| G3 | 11.09%    | 44.32%         |
| G4 | 11.57%    | 42.84%         |

G2: the 0.5 g/kg HC group (oral administration of 0.5 g/kg of 95% ethanol extract of leaves and pseudostems of *Hedychium coronarium* Koening);
G3: the 1.0 g/kg HC group (oral administration of 1.0 g/kg of 95% ethanol extract of leaves and pseudostems of *Hedychium coronarium* Koening);
G4: the 1.5 g/kg HC group (oral administration of 1.5 g/kg of 95% ethanol extract of leaves and pseudostems of *Hedychium coronarium* Koening).

The results show that when compared with the placebo group, the blood glucose levels at intervals of 30, 60 and 90 minutes after administration of glucose were effectively reduced in the 0.5 g/kg HC group. The efficacies of lowering blood glucose were 31%, 44%, 43%, respectively. It also demonstrates that administration of 1.0 g/kg of 95% ethanol extract of leaves and pseudostems of *Hedychium coronarium* Koening is needed to lower blood glucose in normal mice for more than 40%.

Example 23

Figure 16:
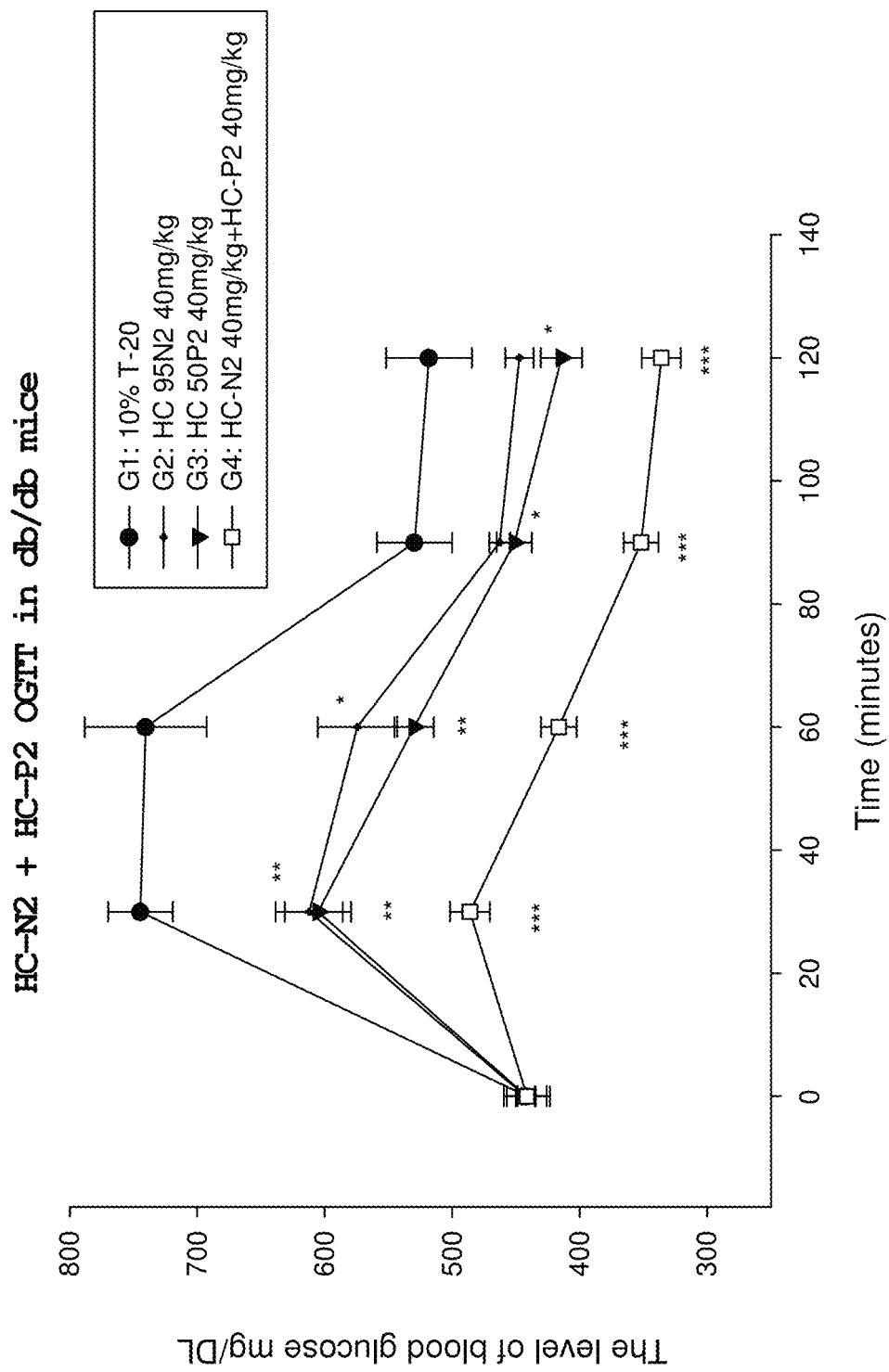
FIG. 16 illustrates the effect of the combined product (DM101), HC-N2 or HC-P2 in $db^+/db^+$ mice with type II diabetes. "G1" indicates oral administration of 10% Tween 20; "G2" indicates oral administration of 40 mg/kg HC-N2; "G3" indicates oral administration of 40 mg/kg HC-P2; and "G4" indicates oral administration of 40 mg/kg HC-N2 plus 40 mg/kg HC-P2 (i.e. DM101). The X axis represents the time intervals of blood sampling, and the Y axis represents the concentration of blood glucose. P values are calculated by t-test of Sigma Statistical Software wherein $p<0.05$ is considered significant and marked with *; $p<0.01$ is considered highly significant and marked with ; and $p\leq0.001$ is considered very highly significant and marked with *.

Oral Glucose Tolerance Test of the Isolated Products, HC-N2 and HC-P2, and the Combined Product DM101 of the Ethanol Extracts of Leaves and Pseudostems of *Hedychium coronarium* Koening in db$^+$/db$^+$ Mice Twenty-four (24) db$^+$/db$^+$ mice with type II diabetes (C57BLKS/J Iar-+Leprdb/+Leprdb) were divided into four groups: the placebo group (6 mice, to be administered with 10% Tween 20), the 40 mg/kg HC-N2 group (6 mice, to be administered with 40 mg/kg HC-N2), the 40 mg/kg HC-P2 group (6 mice, to be administered with 40 mg/kg HC-P2), and 80 mg/kg DM101 group (6 mice, to be administered with 80 mg/kg DM101). The mice were fasted for 14 hours and then allowed to feed freely for 1 hour. After 4 hours, the mice were orally administered with 10% Tween 20 (the placebo group), 40 mg/kg HC-N2 (the 40 mg/kg HC-N2 group), 40 mg/kg HC-P2 (the 40 mg/kg HC-P2 group), and 80 mg/kg DM101 (the 80 mg/kg DM101 group). After 30 minutes, each mouse was orally administered with 2 g/kg glucose. Blood was drawn from each mouse at the intervals of 0, 30, 60, 90, and 120 minutes for the measurement of glucose (mg/DL). The results are shown in the table below and FIG. 16.

| | Concentration of blood glucose (mg/DL) | | | | |
|---|---|---|---|---|---|
| Group | 0 min | 30 min | 60 min | 90 min | 120 min |
| Placebo group (G1) | 441.5 +/− 15.6 | 744.5 +/− 25.3 | 740.5 +/− 47.8 | 529.5 +/− 29.6 | 518.2 +/− 33.7 |
| 40 mg/kg HC-N2 group (G2) | 442.7 +/− 7.6 | 612.2 +/− 26.3** | 574.3 +/− 31.2* | 462.7 +/− 8.2 | 447.2 +/− 11.1 |
| 40 mg/kg HC-P2 group (G3) | 441.7 +/− 7.1 | 605.2 +/− 26.0** | 529.8 +/− 15.4** | 451.2 +/− 13.7* | 414.3 +/− 16.3* |
| 80 mg/kg DM101 group (G4) | 441.3 +/− 18.0 | 486.0 +/− 15.6*** | 416.3 +/− 14.0*** | 351.8 +/− 13.5*** | 336 +/− 15.3*** |

The data is expressed with mean +/− standard error (SEM). P values are calculated by t-test of Sigma Statistical Software, wherein $p < 0.05$ is considered significant and marked with the symbol "*";
$p < 0.01$ is considered highly significant and marked with the symbol "**";
and $p \leq 0.001$ is considered very highly significant and marked with the symbol "***".

Moreover, the resultant percentages of decreased blood glucose are shown below:

| | AUC from 0 min |
|---|---|
| G2 | 55.59% |
| G3 | 66.02% |
| G4 | 116.82% |

G2: the 40 mg/kg HC-N2 group, which was orally administered with 40 mg/kg HC-N2;
G3: the 40 mg/kg of HC-P2 group, which was orally administered with 40 mg/kg HC-P2;
G4: the 80 mg/kg DM101 group, which was orally administered with 80 mg/kg DM101.

The results show that when compared with the placebo group, the blood glucose levels at intervals of 30, 60, 90 and 120 minutes after administration of glucose were very highly significantly reduced in the 80 mg/kg DM101 group; the blood glucose levels at intervals of 30 and 60 minutes after administration of glucose were very significantly reduced and that at intervals of 90 and 120 minutes after administration of glucose were significantly reduced, in the 40 mg/kg HC-N2 group; and the blood glucose levels at intervals of 30, 60, 90 and 120 minutes after administration of glucose were significantly reduced in the 40 mg/kg HC-P2 group. The efficacies of lowering blood glucose were 56% in the 40 mg/kg HC-N2 group, 66% in the 40 mg/kg HC-P2 group, and 117% in the 80 mg/kg DM101 group (lower than that at interval of 0 min), respectively. It also demonstrates that the efficacies of lowering blood glucose of the isolated product, HC-N2 (the isolated product of 95% ethanol extract of leaves and pseudostems of *Hedychium coronarium Koening*, 40 mg/kg) and HC-P2 (the isolated product of 50% ethanol extract of leaves and pseudostems of *Hedychium coronarium Koening*, 40 mg/kg) are 56% and 66%, respectively, and that of the combined product DM101 (80 mg/kg) is 117%.

What is claimed is:

1. A method for preparing a *Hedychium coronarium Koenig* extract (HC extract) useful for treating diabetes, the method comprising:
   (a) extracting an overground part of *Hedychium coronarium Koenig* with a first solvent to obtain a first extract, wherein the first solvent is (i) petroleum ether, (ii) n-hexane, (iii) dichloromethane, (iv) trichloromethane, (v) ethyl acetate, (vi) acetone, or (vii) ethanol at a concentration of 70-100% (v/v in water), or (viii) a combination of any of (i) to (vii),
   (b) loading the first extract onto a first ion exchange chromatography column,
   (c) washing the first ion exchange chromatography column with a solution of water and ethanol at a volume ratio from 1:1 to 1:9, and
   (d) eluting the first ion exchange chromatography column with ethanol at a concentration of at least 70% (v/v in water) to produce the HC extract.

2. The method of claim 1, wherein the overground part of *Hedychium coronarium Koenig* comprises a leaf, a pseudostem, or both.

3. The method of claim 1, wherein the first solvent is 95% ethanol (v/v in water).

4. An extract of *Hedychium coronarium Koenig*, which exhibits four peaks at retention times of (i) 8.55-10.34 minutes, (ii) 17.64-21.34 minutes, (iii) 20.55-24.86 minutes and (iv) 42.91-51.92 minutes in a first high performance liquid chromatography (HPLC) analysis using a linear gradient of methanol and water, wherein the first HPLC analysis is carried out under the following conditions: mobile phase at 0 minute: 66% MeOH/34% $H_2O$; at 60 minute: 100% MeOH/0% $H_2O$; at 76 minute: 100% MeOH/0% $H_2O$; at 78 minutes: 66% MeOH/34% $H_2O$; and at 86 minutes: 66% MeOH/34% $H_2O$; flow rate: 1.0 mL/min; and detection wavelength: 254 nm; wherein the extract is produced by the method of claim 1.

5. The extract of claim 4, which exhibits four peaks at retention times of about 9.4 minutes, about 19.4 minutes, about 22.6 minutes, and about 47.2 minutes in the HPLC analysis.

6. The HC extract of claim 4, which further exhibits five peaks at retention times of (i) 24.45-29.59 minutes, (ii) 29.00-35.09 minutes, (iii) 39.36-47.63 minutes, (iv) 55.82-67.54 minutes, and (v) 63.73-77.11 minutes in a second performance liquid chromatography (HPLC) analysis using a linear gradient of acetonitrile (ACN) and water containing 0.1% trifluoroacetic acid (TFA), wherein the second HPLC analysis is carried out under the following condition: (2) mobile phase at 0 minute: 10% ACN (in 0.05% TFA)/90% $H_2O$ (in 0.05% TFA); at 80 minutes: 17% ACN (in 0.05% TFA)/83% $H_2O$ (in 0.05% TFA); at 90 minutes: 100% ACN (in 0.05% TFA)/0% $H_2O$ (in 0.05% TFA); at 100 minutes: 100% ACN (in 0.05% TFA)/0% $H_2O$ (in 0.05% TFA); at 102 minute: 10% ACN (in 0.05% TFA)/90% $H_2O$ (in 0.05% TFA); and at 110 minute: 10% ACN (in 0.05% TFA)/90% $H_2O$ (in 0.05% TFA); flow rate: 1.0 mL/min; and detection wavelength: 254 nm.

7. A method for treating diabetes in a subject in need thereof, comprising administering to the subject an effective amount of the *Hedychium coronarium Koenig* extract (HC extract) of claim 6.

8. The method of claim 7, wherein the effective amount of the HC extract is sufficient to lower blood glucose levels, increase insulin levels, or reduce insulin resistance of the subject.

9. The method of claim 8, wherein the amount of the HC extract administered to the subject does not lower blood glucose levels of the subject in a fasting state.

10. A method for treating diabetes in a subject in need thereof, comprising administering to the subject an effective amount of the *Hedychium coronarium Koenig* extract (HC extract) of claim 4.

11. The method of claim 10, wherein the effective amount of the HC extract is sufficient to lower blood glucose levels, increase insulin levels, or reduce insulin resistance of the subject.

12. The method of claim 11, wherein the amount of the HC extract administered to the subject does not lower blood glucose levels of the subject in a fasting state.

13. A method for preparing a *Hedychium coronarium Koenig* extract (HC extract) useful for treating diabetes, the method comprising:
  (a) extracting an overground part of *Hedychium coronarium Koenig* with a first solvent to obtain a first residue and a first extract, wherein the first solvent is (i) petroleum ether, (ii) n-hexane, (iii) dichloromethane, (iv) trichloromethane, (v) ethyl acetate, (vi) acetone, or (vii) ethanol at a concentration of at least 70% (v/v in water), or (viii) a combination of any of (i) to (vii);
  (b) extracting the first residue with a second solvent to obtain a second extract, wherein the second solvent is (1) water, (2) ethanol at a concentration of up to 50% (v/v in water), (3) methanol, (4) butanol, (5) iso-butanol, or (6) acetone at a concentration of up to 80% (v/v in water), or (7) a combination of any of (1)-(6);
  (c) loading the second extract onto a second ion exchange chromatography column;
  (d) washing the second ion exchange chromatography column with water; and
  (e) eluting the second ion exchange chromatography column with ethanol at a concentration of 5-50% (v/v in water) to produce the HC extract.

14. The method of claim 13, wherein the overground part of *Hedychium coronarium Koenig* comprises a leaf, a pseudostem, or both.

15. The method of claim 13, wherein the first solvent is 95% ethanol (v/v in water).

16. The method of claim 13, wherein the second solvent is ethanol at a concentration of up to 50% (v/v in water).

17. An extract of *Hedychium coronarium Koenig*, which exhibits five peaks at retention times of (i) 24.45-29.59 minutes, (ii) 29.00-35.09 minutes, (iii) 39.36-47.63 minutes, (iv) 55.82-67.54 minutes, and (v) 63.73-77.11 minutes in a performance liquid chromatography (HPLC) analysis using a linear gradient of acetonitrile (ACN) and water containing 0.1% trifluoroacetic acid (TFA), wherein the HPLC analysis is carried out under the following condition: mobile phase at 0 minute: 10% ACN (in 0.05% TFA)/90% $H_2O$ (in 0.05% TFA); at 80 minutes: 17% ACN (in 0.05% TFA)/83% $H_2O$ (in 0.05% TFA); at 90 minutes: 100% ACN (in 0.05%TFA)/0% $H_2O$ (in 0.05%TFA); at 100 minutes: 100% ACN (in 0.05% TFA)/0% $H_2O$ (in 0.05% TFA); at 102 minute: 10% ACN (in 0.05% TFA)/90% $H_2O$ (in 0.05% TFA); and at 110 minute: 10% ACN (in 0.05% TFA)/90% $H_2O$ (in 0.05% TFA); flow rate: 1.0 mL/min; and detection wavelength: 254 nm; wherein the extract is produced by the method of claim 13.

18. The extract of claim 17, which exhibits five peaks at retention times of about 26.9 minutes, about 31.9 minutes, about 43.3 minutes, about 61.4 minutes, and about 70.1 minutes in the HPLC analysis.

19. A method for treating diabetes in a subject in need thereof, comprising administering to the subject an effective amount of the *Hedychium coronarium Koenig* extract (HC extract) of claim 17.

20. The method of claim 19, wherein the effective amount of the HC extract is sufficient to lower blood glucose levels, increase insulin levels, or reduce insulin resistance of the subject.

21. The method of claim 20, wherein the amount of the HC extract administered to the subject does not lower blood glucose levels of the subject in a fasting state.

22. A method for preparing a *Hedychium coronarium Koenig* extract (HC extract) useful for treating diabetes, the method comprising:
  (a) extracting an overground part of *Hedychium coronarium Koenig* with a first solvent to obtain a first extract and a first residue, wherein the first solvent is (i) petroleum ether, (ii) n-hexane, (iii) dichloromethane, (iv) trichloromethane, (v) ethyl acetate, (vi) acetone, or (vii) ethanol at a concentration of at least 70% (v/v in water), or (viii) a combinations of any of (i) to (vii);
  (b) extracting the first residue with a second solvent to obtain a second extract, wherein the second solvent is (1) water, (2) ethanol at a concentration of up to 50% (v/v in water), (3) methanol, (4) butanol, (5) iso-butanol, or (6) acetone at a concentration of up to 80% (v/v in water), or (7) a combination of any of (1) to (6);
  (c) subjecting the first extract and the second extract to ion exchange chromatography to obtain a first eluate and a second eluate, respectively;
    wherein the first eluate is obtained by a process comprising:
      loading the first extract onto a first ion exchange chromatography column,
      washing the first ion exchange chromatography column with a solution of water and ethanol at a volume ratio from 1:1 to 1:9, and
      eluting the first ion exchange chromatography column with ethanol at a concentration of at least 70% (v/v in water) to produce the first eluate; and
    wherein the second eluate is obtained by a process comprising:
      loading the second extract onto a second ion exchange chromatography column,
      washing the second ion exchange chromatography with water, and
      eluting the second ion exchange chromatography with ethanol at a concentration of 5-50% (v/v in water) to produce the second eluate; and
  (d) combining the first eluate and the second eluate to obtain the HC extract.

23. The method of claim 22, wherein the overground part of *Hedychium coronarium Koenig* comprises a leaf, a pseudostem, or both.

24. The method of claim 22, wherein the first solvent is 95% ethanol (v/v in water).

25. The method of claim 22, wherein the second solvent is ethanol at a concentration of up to 50% (v/v in water).

* * * * *

UNITED STATES PATENT AND TRADEMARK OFFICE
CERTIFICATE OF CORRECTION

PATENT NO. : 9,023,407 B2  
APPLICATION NO. : 13/569656  
DATED : May 5, 2015  
INVENTOR(S) : Wu et al.

Page 1 of 1

It is certified that error appears in the above-identified patent and that said Letters Patent is hereby corrected as shown below:

On the title page item [30], should read

--Taiwan 100128239  08/08/2011--

Signed and Sealed this
Fifteenth Day of September, 2015

Michelle K. Lee
*Director of the United States Patent and Trademark Office*